(12) United States Patent
Summerer et al.

(10) Patent No.: US 9,879,315 B2
(45) Date of Patent: Jan. 30, 2018

(54) DIRECT, PROGRAMMABLE DETECTION OF EPIGENETIC DNA CYTOSINE MODIFICATIONS USING TAL EFFECTORS

(71) Applicant: Universität Konstanz, Constance (DE)

(72) Inventors: Daniel Summerer, Constance (DE); M. Grzegorz Kubik, Constance (DE); Moritz Johannes Schmidt, Constance (DE)

(73) Assignee: Universität Konstanz, Constance (DE)

( * ) Notice: Subject to any disclaimer, the term of this patent is extended or adjusted under 35 U.S.C. 154(b) by 0 days.

(21) Appl. No.: 14/899,483

(22) PCT Filed: Jun. 26, 2014

(86) PCT No.: PCT/EP2014/001753
§ 371 (c)(1),
(2) Date: Dec. 17, 2015

(87) PCT Pub. No.: WO2014/206568
PCT Pub. Date: Dec. 31, 2014

(65) Prior Publication Data
US 2016/0138094 A1 May 19, 2016

(30) Foreign Application Priority Data
Jun. 26, 2013 (EP) .................................. 13003252

(51) Int. Cl.
*C12Q 1/68* (2006.01)
(52) U.S. Cl.
CPC ......... *C12Q 1/6827* (2013.01); *C12Q 1/6858* (2013.01)

(58) Field of Classification Search
None
See application file for complete search history.

(56) References Cited

U.S. PATENT DOCUMENTS

2010/0041057 A1  2/2010  Dong

FOREIGN PATENT DOCUMENTS

| WO | 2012/054730 A1 | 4/2012 |
| WO | 2013/016486 A1 | 1/2013 |

OTHER PUBLICATIONS

Kubik et al. J. Am. Chem. Soc. 2015. 137:2-5.*

(Continued)

*Primary Examiner* — Joseph G. Dauner
(74) *Attorney, Agent, or Firm* — McDonnell Boehnen Hulbert & Berghoff LLP

(57) ABSTRACT

Methods for the differentiation of a 5-hydroxymethyl modification of a cytosine residue of interest in a nucleic acid molecule from (i) a 5-methyl modification of the cytosine residue of interest or (ii) an unmodified cytosine residue of interest, the methods making use of the capability of transcription-activator-like effector (TALE) proteins to preferentially bind with strong affinity to nucleic acid sequences containing non-modified cytosine residues or 5-methyl modified cytosine residues, and to bind, if at all, with only strongly reduced affinity to nucleic acid sequences containing 5-hydroxymethyl modified cytosine residues. The present invention further relates to respective uses of TALE proteins for the differentiation of a 5-hydroxymethyl modification of a cytosine residue of interest in a nucleic acid molecule from (i) a 5-methyl modification of the cytosine residue of interest or (ii) the unmodified cytosine residue of interest.

8 Claims, 20 Drawing Sheets

(56) References Cited

OTHER PUBLICATIONS

Figure 1:
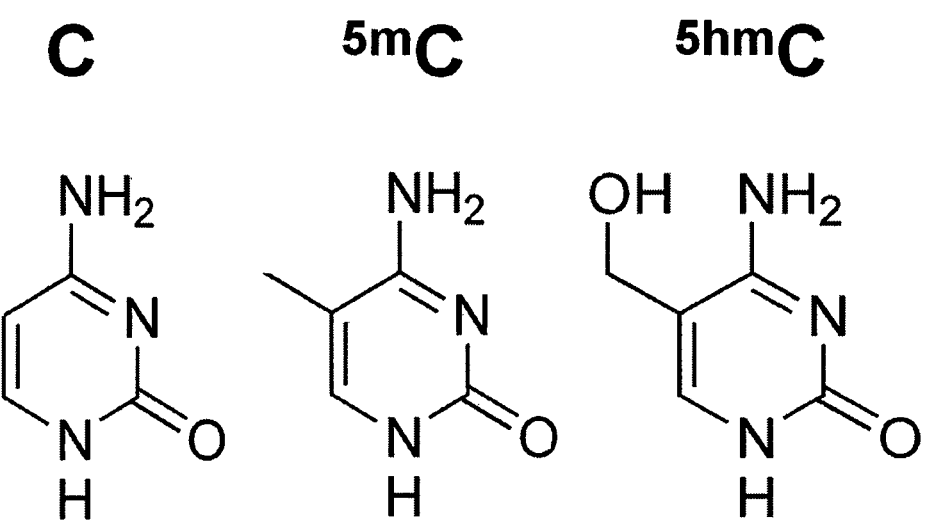

Valton et al. The Journal of Biological Chemistry. 2012. 287(46):38427-38432.*
Jong et al., "Recognition of methylated DNA by TAL Effectors", Cell Research, 22(10):1502-1504 (2012).
Miao et al., "Base-Resolution Analysis of 5-Hydroxymethylcytosine in the Mammalian Genome", Cell, 149(6):1368-1380 (2012).

* cited by examiner

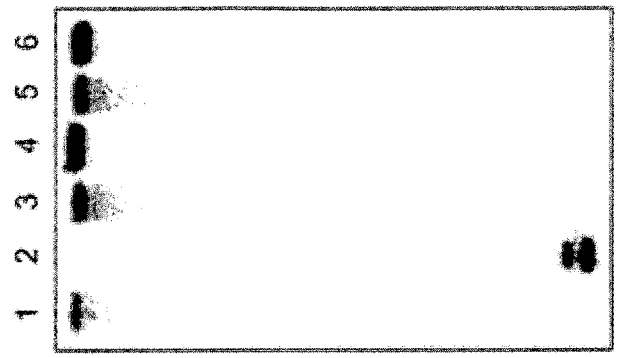
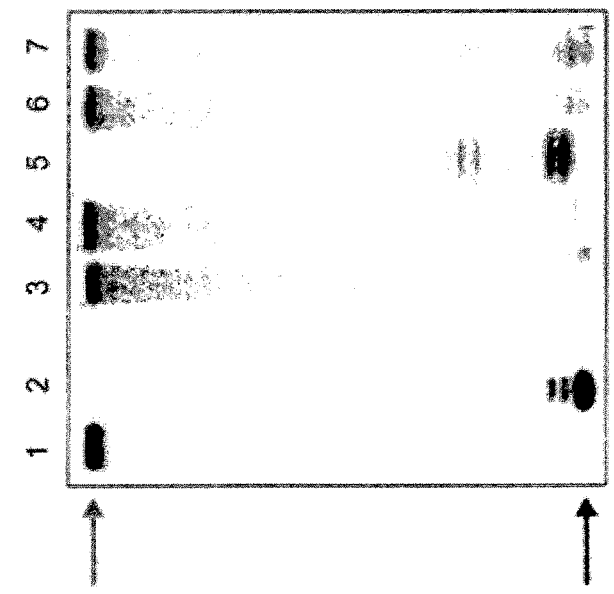
Figure 5B,C

| t97_C6→mC | + | - | + | - | + | - |
|---|---|---|---|---|---|---|
| t97 | - | + | - | + | - | + |
| gDNA in hybridization step [µg/µl] | 0.1 | | 1 | | 10 | |

Amount of Klenow Fragment: 0.125 U each
Incubation time: 15 min each

| t97_C6→mC | + | - | + | - | + | - | + | - | + | - | + | - |
|---|---|---|---|---|---|---|---|---|---|---|---|---|
| t97 | - | + | - | + | - | + | - | + | - | + | - | + |
| Incubation time [h] | 0.5 | | 1 | | 2 | | 3 | | 6 | | 12 | |

Amount of Klenow Fragment: 0.125 U each

Figure 7

| KI values | C | mC | hmC |
|---|---|---|---|
| HD | 50 ± 7 nM | | |
| N* | 60 ± 4 nM | 51 ± 2 nM | ~ 1500 nM |
| NG | 357 ± 33 nM | 163 ± 5 nM | ~ 2000 nM |

DIRECT, PROGRAMMABLE DETECTION OF EPIGENETIC DNA CYTOSINE MODIFICATIONS USING TAL EFFECTORS

The present invention relates to methods for the differentiation of a 5-hydroxymethyl modification of a cytosine residue of interest in a nucleic acid molecule from (i) a 5-methyl modification of said cytosine residue of interest or (ii) said unmodified cytosine residue of interest, said methods making use of the capability of transcription-activator-like effector (TALE) proteins to preferentially bind with strong affinity to nucleic acid sequences containing non-modified cytosine residues or 5-methyl modified cytosine residues, and to bind, if at all, with only strongly reduced affinity to nucleic acid sequences containing 5-hydroxymethyl modified cytosine residues. The present invention further relates to respective uses of TALE proteins for the differentiation of a 5-hydroxymethyl modification of a cytosine residue of interest in a nucleic acid molecule from (i) a 5-methyl modification of said cytosine residue of interest or (ii) said unmodified cytosine residue of interest.

5-Methylcytosine ($^{5m}C$, FIG. 1) is an essential epigenetic DNA modification that acts as an important factor in the silencing of genes. It has important roles in the regulation of gene expression, genome stability and disease including neurological disorders and various cancer types. In recent years, with the development of epigenetics, high importance has been attached to the selective detection of $^{5m}C$ in genes, given the strong correlation of this genetic modification with various aspects of gene control, such as gene regulation, genomic imprinting, and X chromosome inactivation, among other effects. It has been reported that a high level of $^{5m}C$ at CpG islands within promoters and the global hypomethylation of genomic DNA, which induces gene instability, can produce the activation of oncogenes and the high occurrence of various diseases. Thus, methods for the direct assessment of the $^{5m}C$ level and status in genes with high resolution at user-defined genomic loci are of broad interest for diagnosis and therapy, e.g. for the early detection and treatment of many tumors. However, because of the subtle differences between the respective nucleotides containing C or $^{5m}C$ (i.e. deoxycytidine (dC) and 5-methyl-2'-deoxycytidine ($^{5m}dC$)), distinguishing $^{5m}dC$ from dC is a difficult and challenging task.

5-Hydroxymethylcytosine ($^{5hm}C$, FIG. 1) was first discovered in the bacteriophages T2, T4 and T6 in 1952. The presence of it in mammalian DNA was suggested not until twenty years later, but has received only little scientific attention. In 2009, 5-hydroxymethylcytosine was detected in cerebellar Purkinje neurons in the brain. Simultaneously, 5-hydroxymethylcytosine was reported to be present in mouse embryonic stem cells and human embryonic kidney cells. The TET1 (ten-eleven translocation 1) protein, a fusion partner of histone methyltransferase in acute myeloid leukemia, was identified as a 2-oxoglutarate- and Fe(II)-dependent enzyme that catalyses the conversion of 5-methylcytosine to 5-hydroxymethylcytosine in vitro, as well as in cultured cells. Moreover, it has been shown that prokaryotic cytosine-5 methyltransferases were able to produce 5-hydroxymethylcytosine by reversible addition of formaldehyde to cytosine. It was supposed that 5-hydroxymethylcytosine is formed at 5-methylcytosine sites in response to oxidative stress. Further, it has been speculated that 5-hydroxymethylcytosine together with 5-formyldeoxycytosine could be one of the main oxidative degradation products of 5-methylcytosine.

Figure 16:
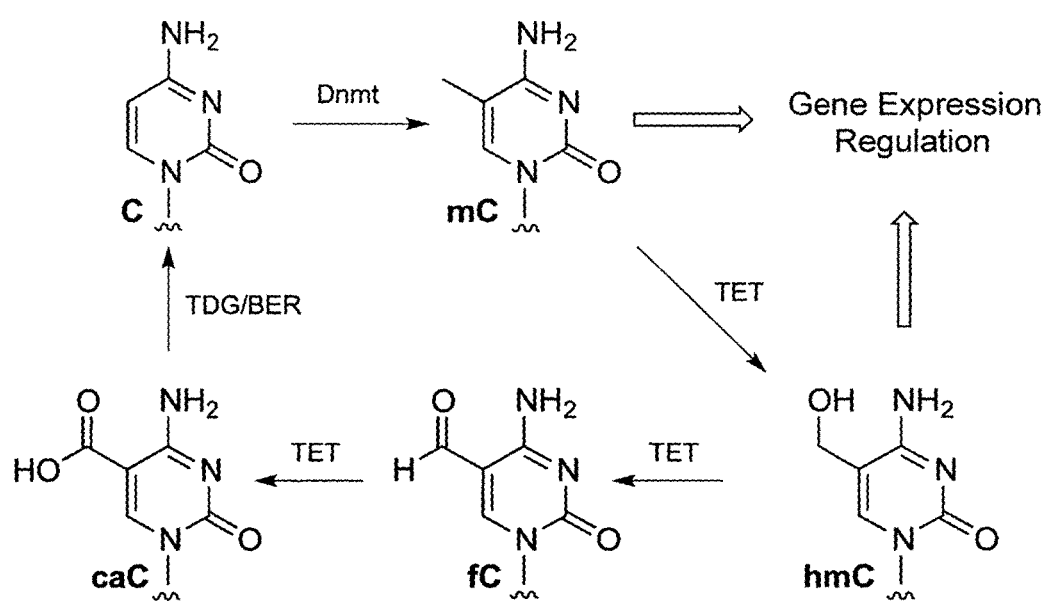

The human body consists of over 200 different cell types with diverse functions, yet with almost identical genomes. This phenotypic diversity is determined by differences in gene expression profiles. Central regulatory elements of gene expression are epigenetic DNA modifications that affect local transcriptional activity of the genome by controlling chromatin structure. In contrast to other, rather transient regulatory elements, epigenetic DNA modifications can be preserved or regenerated during cell division, resulting in inheritable imprinting of regulatory states. Among these, methylation of DNA cytosine (C) residues in CpG dinucleotides at the carbon 5-position (5-Methylcytosine, $^{5m}C$ or mC, FIG. 1, FIG. 16) is the most common modification in vertebrates.

Key to the epigenetic regulation of gene expression is the introduction (methylation, "writing") and removal (de-methylation, "erasing") of methyl-groups. However, while the process of DNA methylation catalyzed by DNA methyltransferases (Dmnt) is well characterized, the process of de-methylation is not and the enzymes that are involved in this process have long remained elusive. As stated above, ten-eleven translocation (TET) family dioxygenases have recently been discovered to oxidize mC to 5-hydroxymethylcytosine ($^{5hm}C$ or hmC, FIG. 1, FIG. 16). hmC is now recognized as key intermediate of mC de-methylation that can either be passively depleted through DNA replication or actively reverted to C, e.g. through iterative oxidation to 5-formylcytosine (fC) and 5-carboxylcytosine (caC) and thymine DNA glycosylase (TDG)-mediated base excision repair (BER, FIG. 16). Methylation, oxidation and repair now offer a model for the long searched, complete cycle of dynamic cytosine modification, with paramount importance for cell development, differentiation, and the onset of diseases including cancer.

In fact, numerous studies have revealed alterations in mC modification patterns between normal and cancer cells that affect transcriptional up- or down-regulation of oncogenes and tumor-suppressor genes, respectively. These data include examples from all classes of human neoplasia and have highlighted the existence of a unique profile of mC that defines each type of cancer. It has thereby been shown that aberrant mC patterns occur early in tumorigenesis, with implications for early detection of cancer. Consequently, mC has become an important biomarker for a large number of cancer tissues. For example, typing promoter methylation in the glutathione S-transferase P1 (GSTP1) and $O^6$-methyl-guanine-DNA methyltransferase (MGMT) genes in prostate cancer and glioma provides excellent perspectives for diagnosis and for determining appropriate therapies.

Importantly, hmC, besides being a de-methylation intermediate, is increasingly recognized to have inherent biological functions on its own, indicated by its unique cell-type specific occurrences, genomic distribution patterns and impact on the binding ability of DNA-binding proteins (in contrast, fC and caC are significantly less abundant and their potential biological roles have yet to be discovered). Indeed, recent studies established hmC and aberrant TET dioxygenase activity as novel biomarkers for various cancers that exhibit large, wide-spread differences in normal and cancer tissue. Moreover, editing of the hmC-landscape in melanoma cells has been shown to even result in suppression of melanoma growth and to increase tumor-free survival in animal models. These data illustrate the considerable potential of mC/hmC analysis as novel approaches for cancer diagnosis.

To date, several initiatives have attempted to address the challenge of $^{5m}C$ detection by indirect detection strategies.

Chemical methods involving the conversion of either C or $^{5m}$C residues in DNA have been proposed. For instance, the Maxam-Gilbert chemical modification was applied to identify the $^{5m}$C residues indirectly by means of the interference of the methyl group in the reaction with hydrazine. Moreover, $OsO_4$ has been assessed as a potential reagent for differentiating between $^{5m}$C and C since $OsO_4$ reacts differently to the distinct nucleophilicities of the double bonds in $^{5m}$C and C. However, the $OsO_4$ technique cannot address situations involving the oxidation of thymidines. Other combinations, such as the $V_2O_5$/LiBr or $NaIO_4$/LiBr pairings and N-Halogeno-N-sod iobenzenesulfonamide reagents, have partially solved the aforementioned detection difficulties, but the sensitivity of these assays requires additional improvement.

Various methods based on indirect detection of $^{5m}$C after conversion of the sample DNA with bisulfite have been developed and are currently the gold standard. These include methyl-specific PCR (MSP), bisulfite Sanger sequencing, pyrosequencing and next-generation sequencing, microarray-based methods and others. However, bisulfite treatment is time-consuming and cumbersome, can harm the sample and results in reduction of sequence complexity, which complicates analysis. Further, direct approaches based on enzymatic reactions and/or selective binding have been developed utilizing a range of methyl-CpG-binding domains, antibodies or restriction enzymes, but these suffer from the poor modularity and constraints of sequence recognition of employed proteins and are thus neither flexible nor specific for single target sites. Furthermore, even the single molecule real time sequencing (SMRT) technique, which can directly detect DNA methylation without bisulfite conversion, possesses the problem of a high error rate and is technically extremely demanding.

The paramount importance of dynamic, epigenetic modification of cytosine has created a considerable need for methods that can delineate both regional patterns (typing) and broader profiles (profiling) of C-modification in genomes. These have important implications for understanding why specific regions of a genome can be expressed in different developmental contexts and how epigenetic changes enable aberrant expression patterns and the onset of disease. In particular, the identification of a vast number of mC positions as cancer biomarkers (and the emerging role of hmC in the same context) has opened excellent perspectives for cancer diagnosis, prognosis and the determination of suited therapies in mass applications.

Consequently, a large number of different C-modification typing and profiling assays have been developed. These however rely on only few, highly limited and complicated strategies to address the molecular key step of any such approach, which is the differentiation of the nucleobases C, mC and hmC. These limitations arise from the inferior analytic accessibility of epigenetic C-modifications compared to modifications of the DNA sequence itself: unlike DNA sequence information that can be reliably amplified, transcribed or cloned, DNA epigenetic information is erased by such molecular biology techniques, and it is not revealed by Watson-Crick-hybridization. Therefore, C-modification-dependent pretreatments of DNA were developed for differentiation. After genomic DNA has been treated, various molecular biology techniques including qPCR and DNA sequencing can be used to reveal the location of C-modifications.

A major group of differentiation approaches is based on chemical conversion, i.e. on the selective deamination of C (but not mC/hmC) with bisulfite and subsequent analysis of the resulting C to uridine (U) mutation. This can be coupled with additional conversion steps to achieve a partial selectivity between C, mC and hmC. For example, oxidation with $KRuO_4$ converts hmC to fC, whereas mC remains unchanged. fC is converted to U in bisulfite treatments, and thus hmC and mC can be indirectly differentiated in comparative assays. Alternatively, hmC can be glycosylated and then reads as C after bisulfite treatment. If this is coupled with an oxidation step using a TET dioxygenase, all other C-modifications will be oxidized to caC and then read as U after bisulfite treatment.

Though bisulfite-based approaches have been widely used since more than 20 years, they suffer from severe drawbacks: Despite extensive optimization efforts, the conversion is still laborious and time-consuming (i.e. 4-16 h without subsequent DNA purification). The applied conditions are harsh and can lead to the destruction of ~95% of the sample DNA. Moreover, the sequence complexity of the sample is widely reduced to only three nucleotides (A, G, U(T)), because of the C to U conversion. This strongly reduces the selectivity of Watson-Crick hybridization (e.g. in PCR, sequencing or microarrays) and consequently often requires tedious optimization of downstream analyses. Moreover, the reduction interferes with bio-informatic alignments. These drawbacks prevent in vivo applications and severely complicate the development of straightforward cancer diagnostic assays.

A second group of differentiation approaches relies on proteins that bind (and potentially modify) C-modifications directly, i.e. without chemical conversion. However, proteins that are currently employed for this (e.g. antibodies, restriction enzymes, β-glucosyltransferase) exhibit no or constraint sequence-selectivity. This prevents their use for direct, locus-specific differentiation and thus they require the coupling to sequence-selective downstream analyses.

As a third group of differentiation approaches, protein nanopores and DNA polymerases have recently been introduced. These act as "processive readers", i.e. they offer the direct and combined analysis of DNA sequence and C-modifications in a processive manner. However, though highly appealing for sequencing, these approaches are technically demanding and restricted to single molecule techniques in vitro. Moreover, they require DNA pretreatments for high confidence analysis.

In fact, none of the available approaches provides inherent, programmable sequence selectivity. This severely complicates in vitro analyses and does not provide perspectives for in vivo applications, since it is not possible to directly differentiate C and C-modifications at user-defined genomic loci.

In view of the aforementioned problems with traditional detection methods, it is vitally important to develop rapid and sensitive methods for the direct, accurate detection of cytosine 5-modifications such as $^{5m}$C and $^{5hm}$C in nucleic acid molecules at user-defined genomic loci.

Accordingly, the technical problem underlying the present invention is to provide improved methods for the differentiation of a 5-hydroxymethyl modification of a cytosine residue of interest in a nucleic acid molecule from (i) a 5-methyl modification of said cytosine residue of interest or (ii) said unmodified cytosine residue of interest, wherein said methods should not compromise the integrity of the nucleic acid molecule and should be fast, easy, sequence- and locus-specific and highly sensitive.

The solution to the above technical problem is achieved by the embodiments characterized in the claims.

In particular, in a first aspect, the present invention relates to a method for the differentiation of a 5-hydroxymethyl modification of a cytosine residue of interest in a nucleic acid molecule from
(i) a 5-methyl modification of said cytosine residue of interest or
(ii) said unmodified cytosine residue of interest,
said method comprising the steps of:
(a) providing a transcription-activator-like effector (TALE) protein, said TALE protein being capable of binding in a sequence- and locus-specific manner to a region of said nucleic acid molecule that includes said cytosine residue of interest; and
(b) determining whether said TALE protein binds to said region;
wherein
(i) a 5-hydroxymethyl modification of said cytosine residue of interest is present when said TALE protein does not bind to said region or does bind to said region with a strongly reduced affinity, and
(ii) a 5-methyl modification of said cytosine residue of interest or said unmodified cytosine residue of interest is present when said TALE protein binds to said region.

In preferred embodiments of the method of the present invention, the repeat variable diresidue (RVD) of said TALE protein whose position corresponds to the position of the cytosine residue of interest is a sized reduced RVD. As used herein, the term "sized reduced RVD" relates to RVDs that are sterically smaller in size than RVDs having an average steric size. In particular, size reduced RVDs can have a deletion of 1, 2, 3, 4, 5, 6, 7, 8, 9, or 10 amino acids. Preferably, size reduced RVDs comprise RVDs X*, wherein X is any proteinogenic amino acid, preferably the RVDs H* and N*, wherein N* is particularly preferred (*=aa deletion).

According to the present invention, a 5-hydroxymethyl modification of a cytosine residue of interest can be differentiated from (i) a 5-methyl modification of said cytosine residue of interest or (ii) said unmodified cytosine residue of interest without the need for any pretreatment or exogenous chemical modification of the nucleic acid molecule. Accordingly, the method of the present invention is significantly less time-, labor- and cost-intensive compared to methods known in the art relying on pretreatments or exogenous chemical modification of the nucleic acid molecule. Moreover, the method of the present invention is highly sensitive and thus allows the detection with high resolution, i.e. differentiation of the modification at single cytosine sites. Finally, the method allows the differentiation at user-defined sites, owing to the programmability of sequence recognition of TALE proteins that exceeds the programmability of any other known protein.

The term "differentiation" as used herein indicates the fact that the method of the present invention allows to determine whether a particular cytosine residue of interest is (i) 5-hydroxymethyl modified, or (ii) 5-methyl modified or unmodified. In particular, binding of the TALE protein to the region of said nucleic acid molecule that includes said cytosine residue of interest indicates that said cytosine residue of interest is 5-methyl modified or unmodified, whereas lack of binding or binding with a strongly reduced affinity indicates that said cytosine residue of interest is 5-hydroxymethyl modified.

According to the present invention, the nucleic acid molecule may be single-stranded or double-stranded. In a preferred embodiment, the nucleic acid molecule is a DNA molecule, more preferably a double-stranded DNA molecule. Further, in accordance with the above, in a preferred embodiment, said nucleic acid molecule is in its native state and is not chemically modified by any pretreatment.

The cytosine residue modifications described herein are physiological cytosine modifications known in the art. In particular, said modifications are 5-methylation or 5-hydroxymethylation of said cytosine residue. Respectively modified cytosine residues are labeled herein as $^{5m}$C or mC for 5-methylcytosine, and as $^{5hm}$C or hmC for 5-hydroxymethylcytosine.

The term "cytosine residue of interest" as used herein points to the fact that with the method of the present invention, any particular cytosine residue in a given nucleic acid molecule can be analyzed for differentiating the modification of said particular residue. This is achieved by providing a TALE protein in step (a) of said method which is capable of binding in a sequence- and locus-specific manner to a region of said nucleic acid molecule that includes said cytosine residue of interest.

In this context, TALE proteins (TALEs) to date represent the protein scaffold with the highest modularity and flexibility of sequence- and locus-specific nucleic acid recognition. They consist of concatenated single modules that each recognize one nucleotide in the target nucleic acid. These modules can be flexibly connected to recognize any arbitrary nucleic acid sequence of interest. The recognition is achieved by only two amino acid residues (repeat variable diresidue, RVD) within each module, providing a "code" of recognition. The most widely used TALE codes are NG for T, NI for A, NN, NK, NH and HN for G and HD for C. RVD HD interacts with C through a hydrogen bond between the aspartate carboxyl group and the nucleobase 4-amino group. It has been shown that the 5-methylation or 5-hydroxymethylation status of C influences the binding of modules containing the HD code, i.e. affinity is strongly reduced, when a modified C instead of an unmodified C is present in the target sequence.

As indicated above, TALEs consist of concatenated modules, each of which recognizes a canonical nucleobase in DNA and this recognition mode is fully programmable. Certain natural or designed TALE modules provide selectivity for mC or hmC and can also provide universality of binding several C-modifications. This makes TALEs the first molecules that hold potential for the direct, fully programmable differentiation of individual C-modifications both in vitro and in vivo. This offers considerable simplifications and performance improvements for typing/profiling in vitro as compared to current approaches.

TALE proteins have recently been discovered as a new scaffold for the design of DNA binding domains with programmable sequence selectivity. Besides fixed N- and C-terminal domains, TALEs feature a central DNA-binding domain that consists of concatenated, interchangeable modules each of which recognizes one of the four canonical DNA nucleotides. These modules consist of 34 amino acids (aa) arranged in two α-helices connected by a small loop. Most of these aa are highly conserved, whereas two aa of the loop are variable (the repeat variable diresidue, RVD) and are responsible for selective nucleobase binding. In the majority of natural TALEs, aa 12 (numbering in the module) is an H or N residue (one-letter aa code) that makes a stabilizing intra-loop hydrogen bond. The second residue (aa 13) makes a specific contact to the edge of the nucleobase through the major groove of the DNA duplex. This results in a winding of the TALE into the DNA groove, forming a super-helical structure, where consecutive TALE modules bind all nucleotides of the forward DNA strand. The nucleotide recognition by TALE RVDs follows a simple code, with the RVDs NI, NN, HD and NG binding the nucleotides A, G, C, and T, respectively. The programmability of TALEs by facile concatenation of individual modules has extensively been proven in various sequence contexts and does not exhibit pronounced context dependencies or sequence constraints.

This fully programmable and selective recognition of canonical nucleobases by TALEs allows the selective recognition of epigenetically modified nucleobases, i.e. C-modifications. This provides a simultaneous, programmable recognition of both DNA sequence and epigenetic C-modification state and thus supersedes any pretreatments that are currently required for differentiation of C-modifications. Indeed, reduced DNA-binding of TALEs is seen at mC- or hmC-containing target sequences.

Interestingly, RVD NG binds mC better than C, and size reduced RVDs, in particular RVD N* (*=aa deletion), bind C and mC with comparable affinities. This demonstrates that it is possible to design universal TALE modules that are able to ignore certain C-modifications at user-defined positions of a target. The present invention further expands this concept from mC to hmC. In particular, a strong differentiation between hmC and mC/C by size reduced RVDs, in particular RVD N*, and between hmC/C and mC by RVD NG was discovered.

More specifically, the 5-hydroxymethylation status of C influences the binding of modules containing size reduced RVDs, in particular the N* code, i.e. affinity is strongly reduced when hmC instead of unmodified C or mC is present in the target sequence. This shows for the first time that TALE modules can be designed that enable differentiation not only between C and mC, but between all three targeted C-modifications including the fully selective sensing of hmC according to the present invention. In fact, TALEs containing designer TALE modules with size reduced RVDs, in particular with RVD H* and/or N* represent the first programmable readers for the selective sensing of hmC.

Thus, in the method of the present invention, TALE proteins can be designed that are capable of binding in a sequence- and locus-specific manner to a region of said nucleic acid molecule that includes said cytosine residue of interest. In this context, the term "capable of binding in a sequence- and locus-specific manner to a region of said nucleic acid molecule that includes said cytosine residue of interest" as used herein relates to the fact that the TALE protein is capable of binding to said region in case the cytosine residue of interest is not modified or 5-methyl modified. In other words, said term relates to the fact that the TALE protein's sequence specificity is directed to the nucleotide sequence of said region wherein the cytosine residue of interest is not modified or 5-methyl modified. In a preferred embodiment, the region to which said TALE protein is capable of binding in a sequence-specific manner is from 10 to 30 nucleotides in length, more preferably from 12 to 28 nucleotides in length, and most preferably from 14 to 24 nucleotides in length. Modification of said cytosine residue by 5-hydroxymethylation strongly reduces the affinity of the binding of said TALE protein to said region. Methods for the design and expression of TALE proteins are not particularly limited and are known in the art.

In this context, it should be noted that under certain conditions, TALE proteins can bind to a nucleic acid molecule containing a cytosine residue that is 5-hydroxymethyl modified, although with a strongly reduced affinity as compared to the binding to the same nucleic acid molecule containing a cytosine residue that is not modified or 5-methyl modified. Therefore, in a preferred embodiment, step (b) of the method of the present invention is performed under conditions that (i) do not allow the binding of the TALE protein to the nucleic acid molecule containing a 5-hydroxymethyl modified cytosine residue, but (ii) allow the binding of the TALE protein to the nucleic acid molecule containing a cytosine residue that is not modified or 5-methyl modified. Respective conditions are known and can be chosen by the person skilled in the art.

The term "strongly reduced affinity" as used herein relates to the effect described above, i.e. that TALE proteins bind to a nucleic acid molecule that does not contain a modified cytosine residue or contains a 5-methyl modified cytosine residue with a first affinity, and bind, if at all, to the same nucleic acid molecule wherein said cytosine residue is 5-hydroxymethyl modified with a second affinity, wherein said second affinity is strongly reduced as compared to said first affinity.

Preferably, said second affinity is 20%, more preferably 10%, more preferably 5%, more preferably 2%, and most preferably 1% or less of said first affinity.

Methods for determining whether the TALE protein binds to said region or does not bind to said region or does bind to said region with a strongly reduced affinity are not particularly limited and are known in the art. In this context, said methods are preferably performed at conditions that (i) do not allow the binding of the TALE protein to the nucleic acid molecule containing a 5-hydroxymethyl modified cytosine residue, but (ii) allow the binding of the TALE protein to the nucleic acid molecule containing a cytosine residue that is not modified or a cytosine residue that is 5-methyl modified. Respective conditions are known and can be chosen by the person skilled in the art.

In a preferred embodiment, the method of the present invention further comprises the step of:
(c) detecting a 5-hydroxymethyl modification of said cytosine residue of interest, wherein
  (i) said modification is present when said TALE protein does not bind to said region or does bind to said region with a strongly reduced affinity, and
  (ii) said modification is absent when said TALE protein binds to said region,
said method allowing for the direct detection of a 5-hydroxymethyl modification of said cytosine residue of interest in said nucleic acid molecule.

As used herein, the terms "direct detection" or "directly detecting" relate to the fact that with the method of the present invention, 5-hydroxymethyl modification of a cytosine residue of interest in a nucleic acid molecule can be detected without the need for any pretreatment or exogenous chemical modification of the nucleic acid molecule.

In a preferred embodiment, step (b) of the method of the present invention comprises the step of determining whether a specific DNA polymerase reaction using a primer that is capable of binding to the region of said nucleic acid molecule that includes said cytosine residue of interest is inhibited, thus indicating binding of said TALE protein to said region, said method allowing for the direct detection of a 5-hydroxymethyl modification of said cytosine residue of interest in said nucleic acid molecule. In this context, binding of the TALE protein to a nucleic acid molecule containing a cytosine residue that is 5-hydroxymethyl modified, i.e. binding with a strongly reduced affinity, does not inhibit the above specific DNA polymerase reaction using a primer that is capable of binding to the region of said nucleic acid molecule that includes said cytosine residue of interest. More preferably, step (b) of the method of the present invention comprises the steps of:

(b1) providing a primer that is capable of binding to the region of said nucleic acid molecule that includes said cytosine residue of interest;
(b2) adding said TALE protein to a first aliquot of the nucleic acid molecule;
(b3) performing a first specific DNA polymerase reaction with said primer using said first aliquot of the nucleic acid molecule as template, and performing a second specific DNA polymerase reaction with said primer using a second aliquot of the nucleic acid molecule as template to which no TALE protein has been added;
(b4) determining at least one parameter, selected from the group consisting of the concentration, size, and sequence of each of the products of said first and second specific DNA polymerase reaction; and
(b5) determining whether said TALE protein binds to said region, wherein
  (i) said TALE protein does not bind to said region or does bind to said region with a strongly reduced affinity when the parameter detected in step (e) for the first specific DNA polymerase reaction does not differ significantly from the parameter detected in step (e) for the second specific DNA polymerase reaction, and
  (ii) said TALE protein binds to said region when the parameter detected in step (e) for the first specific DNA polymerase reaction differs significantly from the parameter detected in step (e) for the second specific DNA polymerase reaction.

In this context, in a particularly preferred embodiment, the method of the present invention comprises the steps of:
(a) providing a transcription-activator-like effector (TALE) protein, said TALE protein being capable of binding in a sequence- and locus-specific manner to a region of said nucleic acid molecule that includes said cytosine residue of interest;
(b1) providing a primer that is capable of binding to the region of said nucleic acid molecule that includes said cytosine residue of interest;
(b2) adding said TALE protein to a first aliquot of the nucleic acid molecule;
(b3) performing a first specific DNA polymerase reaction with said primer using said first aliquot of the nucleic acid molecule as template, and performing a second specific DNA polymerase reaction with said primer using a second aliquot of the nucleic acid molecule to which no TALE protein has been added as template;
(b4) determining at least one parameter, selected from the group consisting of the concentration, size, and sequence of each of the products of said first and second specific DNA polymerase reaction;
(b5) determining whether said TALE protein binds to said region, wherein
  (i) said TALE protein does not bind to said region or does bind to said region with a strongly reduced affinity when the parameter detected in step (e) for the first specific DNA polymerase reaction does not differ significantly from the parameter detected in step (e) for the second specific DNA polymerase reaction, and
  (ii) said TALE protein binds to said region when the parameter detected in step (e) for the first specific DNA polymerase reaction differs significantly from the parameter detected in step (e) for the second specific DNA polymerase reaction; and
(c) detecting said modification of said cytosine residue of interest, wherein
  (i) said modification is present when said TALE protein does not bind to said region or does bind to said region with a strongly reduced affinity, and
  (ii) said modification is absent when said TALE protein binds to said region.

In particularly preferred embodiments of this method, the repeat variable diresidue (RVD) of said TALE protein whose position corresponds to the position of the cytosine residue of interest is a sized reduced RVD, preferably the RVD H* or N*.

In step (b2) of the method of the present invention, the TALE protein is added to the DNA molecules in a molar ratio of TALE protein to DNA of between 2:1 and 500:1, more preferably of between 30:1 to 70:1, more preferably of between 40:1 to 60:1, and most preferably of 50:1.

In step (b3) of the method of the present invention, two separate specific DNA polymerase reactions are performed with the primer of step (b1), the first one using said DNA molecule to which said TALE protein has been added as template, and the second one using said DNA molecule to which no TALE protein has been added as a template. In this context, it has been found that binding of a TALE protein to the region of DNA to which the primer binds abolishes the ability of a DNA polymerase to bind to the DNA-primer complex, thus inhibiting the elongation of the primer. Therefore, in case no modification of the cytosine residue of interest is present, or a 5-methyl modification of the cytosine residue of interest is present, the TALE protein binds to the DNA molecule in the first specific DNA polymerase reaction, thus inhibiting primer extension, whereas in the second specific DNA polymerase reaction, primer elongation occurs. Accordingly, in case a 5-hydroxymethyl modification of the cytosine residue of interest is present, the TALE protein does not bind to the DNA molecule or does bind to said molecule with a strongly reduced affinity in the first specific DNA polymerase reaction, and primer elongation can occur in the same manner as in the second specific DNA polymerase reaction. Suitable DNA polymerase reactions are not particularly limited and are known in the art. They include for example primer extension reaction, arrayed primer extension (APEX), polymerase chain reaction (PCR), rolling circle amplification (RCA) and strand displacement amplification (SDA).

In order to detect whether (i) primer elongation has occurred in both the first and second specific DNA polymerase reaction of step (b3), thus indicating the presence of a 5-hydroxymethyl modification of the cytosine residue of interest, or (ii) primer elongation has occurred only in the second specific DNA polymerase reaction but not in the first, thus indicating the absence of a modification of the cytosine residue of interest or the presence of a 5-methyl modification of said cytosine residue, at least one parameter, selected from the group consisting of the concentration, size (expressed as molecular weight or as chain-length), and sequence, of each of the products of said first and second specific DNA polymerase reaction is determined in step (b5) of the method of the present invention. Methods for the detection of the above parameters are not particularly limited and are known in the art. In a preferred embodiment, in step (b4) of the method of the present invention, (i) the concentration of the products of said first and second specific DNA polymerase reaction is determined using a method, selected from the group consisting of quantitative polymerase chain reaction (qPCR), fluorescence measurements using nucleic acid binding fluorescent probes, and photometry; and/or (ii) the size of the products of said first and second specific DNA polymerase reaction is determined using a method, selected from the group consisting of polymerase chain reaction (PCR), and gel electrophoresis; and/or (iii) the sequence of the products of said first and second specific DNA polymerase reaction is determined using a method, selected from the group consisting of Sanger sequencing, pyrosequencing, microarray hybridization, next-generation sequencing methods, and next-next-generation sequencing methods, including sequence-by-synthesis, sequencing-by-ligation, single molecule sequencing in zero-mode waveguides and nanopore sequencing.

In a particularly preferred embodiment, in step (b4) of the method of the present invention, the concentration of the products of said first and second specific DNA polymerase reaction is determined by qPCR, the primer of step (b1) is biotinylated, and said products are isolated prior to said step (b4) by a method, comprising the steps of:
(i) incubating said products with beads that are coupled to streptavidin;
(ii) removing non-biotinylated template by washing in a buffer that denatures nucleic acid duplexes; and
(iii) using said beads having the biotinylated products bound thereto in said qPCR.

Respective methods of generating biotinylated DNA polymerase reaction products by using biotinylated primers, of isolating biotinylated products using beads that are coupled to streptavidin, and of removing nucleic acid duplexes are not particularly limited and are known in the art. In preferred embodiments, said primer is 5'-biotinylated, said beads are streptavidin-agarose beads, and the buffer used for washing is a buffer containing 20 mM NaOH.

In steps (b5) and (c) of the method of the present invention, the presence or absence of a 5-hydroxymethyl modification of the cytosine residue of interest is actually detected. This is based on the above finding that primer elongation in the first specific DNA polymerase reaction can only occur in case the TALE protein does not bind to the DNA molecule or does bind to said molecule with a strongly reduced affinity, i.e. in case a respective 5-hydroxymethyl modification is present. Thus, in this case the parameter determined in step (b4) will not differ between the first and second specific DNA polymerase reaction. In case a respective modification is not present or a 5-methyl modification is present, the TALE protein will bind to the DNA molecule, thus inhibiting primer elongation, so that the parameter determined in step (b4) will differ between the first and second specific DNA polymerase reaction. In this context, the term "differ significantly" as used herein relates to a difference of at least 10%, preferably at least 20%, at least 30% or at least 50%.

The method of the present invention can not only be used to gain a qualitative result concerning the presence or absence of a 5-hydroxymethyl cytosine modification, but also to gain a quantitative result concerning the degree of 5-hydroxymethyl cytosine modification. To this end, a calibration curve using nucleic acid molecules having a known degree of 5-hydroxymethyl cytosine modification can be established, and the degree of 5-hydroxymethyl cytosine modification of the nucleic acid molecule of interest can be determined by linear regression. Accordingly, in a preferred embodiment, the method of the present invention further comprises the steps of:
(d) comparing the parameter detected in step (b4) for the first specific DNA polymerase reaction to one or more respective parameters obtained from nucleic acid molecules having a known degree of 5-hydroxymethyl modification of the cytosine residue of interest; and
(e) thereby determining the degree of 5-hydroxymethyl modification of the cytosine residue of interest in the nucleic acid molecule.

According to the present invention, the TALE protein provided in step (a) of the method is designed in a way that the RVD whose position corresponds to the position of said cytosine residue of interest, i.e. the RVD that binds to the cytosine of interest in case said cytosine is not modified or is 5-methyl modified, is a size reduced RVD, in particular the RVD H* or N*. As size reduced RVDs, in particular the RVD H* or N*, have a high binding affinity to C and to mC, but a strongly reduced binding affinity to hmC, this allows the detection of hmC in accordance with the method of the present invention as defined above.

The TALE proteins employed in the present invention do not only allow for the differentiation of 5-hydroxymethyl modified cytosine residues from unmodified or 5-methyl modified cytosine residues, but can also be used for a wide range of applications for the detection, manipulation, purification, and analysis of 5-hydroxymethyl modified cytosine residues in nucleic acids. To this end, said TALE proteins can be coupled to a variety of compounds, proteins, affinity ligands, and other moieties. Such "coupling moieties" are not particularly limited and can be easily chosen by a person skilled in the art in accordance with the particular application of interest. Examples of such moieties include fluorescent dyes, fluorescent proteins such as e.g. green fluorescent protein (GFP), affinity ligands such as e.g. biotin, digoxigenin, dinitrophenol, magnetic particles, antibodies, including antibody fragments and antibody mimetics known in the art, and protein tags, and proteins having enzymatic activities such as nuclease activities. Suitable protein tags in this respect include 18A-Tag, ACP-Tag, Avi-Tag, BCCP-Tag, Calmodulin-Tag (CaM-Tag), Chitin-binding-Protein-Tag (CBP-Tag), E-Tag, ELK16-Tag, ELP-Tag, FLAG-Tag, Flash-Tag, poly-glutamic acid-Tag, Glutathion-S-Transferase-Tag (GST-Tag), Green fluorescent protein-Tag (GFP-Tag), Härnagglutinin-Tag (HA-Tag), poly-Histidin-Tag (His-Tag), Isopeptag, Maltose binding protein-Tag (MBP-Tag), Myc-Tag, Nus-Tag, ProtA-Tag, ProtC-Tag, S-Tag, SBP-Tag, Snap-Tag, SpyTag, SofTag 1 and 3, Streptavidin-Tag (Strep-Tag), Strep-II-Tag, Tandem Affinity Purification-Tag (TAP-Tag), TC-Tag, Thioredoxin-Tag (TRX-Tag), Ty-Tag, V5-Tag, VSV-Tag, and Xpress-Tag, which are known in the art. Such "coupling moieties" can be coupled directly or indirectly to the TALE protein, or can be expressed as part of conjugate proteins comprising also the TALE protein. Methods for the coupling of respective "coupling moieties" and for the expression of respective conjugates are not particularly limited and are known in the art. They include methods employing a His-Tag on the expressed conjugates and purification via NiNTA as known in the art.

Applications of respectively coupled TALE proteins are not particularly limited and can be easily devised by the person skilled in the art in accordance with the respective application or scientific problem to be addressed.

In accordance with the above, in a preferred embodiment of the method of the present invention, the TALE protein is coupled directly or indirectly to an affinity ligand, said method further comprising the step of:
(c) depleting nucleic acid molecules in which a 5-methyl modification of said cytosine residue of interest or said unmodified cytosine residue of interest is present via affinity chromatography using said affinity ligand;
said method allowing for the enrichment of nucleic acid molecules in which a 5-hydroxymethyl modification of said cytosine residue of interest is present.

Affinity ligands for use according to this embodiment are not particularly limited and are known in the art. They include for example biotin, digoxigenin, dinitrophenol, magnetic particles, antibodies, including antibody fragments and antibody mimetics, and protein tags, e.g. as indicated above. Methods for the direct or indirect coupling of affinity ligands to TALE proteins are not particularly limited and are known in the art. In this context, the term "coupled directly or indirectly" expressly includes the expression of conjugate molecules of TALE proteins and any particular proteinaceous affinity ligands. Further, the term "coupled indirectly" includes any coupling strategies employing linkers, binding via further affinity partners, and the like, which are known in the art. Moreover, methods for the depletion of nucleic acid molecules in which a 5-methyl modification of said cytosine residue of interest or said unmodified cytosine residue of interest is present via affinity chromatography using said affinity ligands are not particularly limited and are known in the art. Particular methods include the use of His-tags as affinity ligand and depletion of nucleic acids bound to respective TALE proteins via NiNTA-beads, as well as the use of other protein tags as indicated above in connection with the respective affinity binding partners.

According to this embodiment of the method of the present invention, nucleic acid molecules in which a 5-methyl modification of said cytosine residue of interest and/or said unmodified cytosine residue of interest is present are depleted from a mixture containing nucleic acids in which a 5-hydroxymethyl modification of the cytosine residue of interest is present, as well as nucleic acids in which a 5-methyl modification of said cytosine residue of interest is present and/or in which the cytosine residue of interest is not modified. In this manner, nucleic acids in which a 5-hydroxymethyl modification of the cytosine residue of interest is present are enriched in the mixture.

Also in accordance with the above, in a further preferred embodiment of the method of the present invention, the TALE protein is coupled directly or indirectly to a protein having nuclease activity, said method further comprising the step of:
(c) digesting nucleic acid molecules in which a 5-methyl modification of said cytosine residue of interest or said unmodified cytosine residue of interest is present using said protein having nuclease activity;
said method allowing for the differential digestion of nucleic acid molecules in which a 5-methyl modification of said cytosine residue, of interest or said unmodified cytosine residue of interest is present, wherein nucleic acid molecules in which a 5-hydroxymethyl modification of said cytosine residue of interest is present remain undigested.

Proteins having nuclease activity for use according to this embodiment are not particularly limited and are known in the art. They include for example restriction enzymes and cleavage domains of restriction enzymes, e.g. the cleavage domain of FokI. Methods for the direct or indirect coupling of proteins having nuclease activity to TALE proteins are not particularly limited and are known in the art. In this context, the term "coupled directly or indirectly" expressly includes the expression of conjugate molecules of TALE proteins and any particular proteins having nuclease activity. Further, the term "coupled indirectly" includes any coupling strategies employing linkers, binding via further affinity partners, and the like, which are known in the art. Moreover, methods for the digestion of nucleic acid molecules in which a 5-methyl modification of said cytosine residue of interest or said unmodified cytosine residue of interest is present using said proteins having nuclease activity are not particularly limited and are known in the art.

According to this embodiment of the method of the present invention, nucleic acid molecules in which a 5-methyl modification of said cytosine residue of interest and/or said unmodified cytosine residue of interest is present are digested in a mixture containing nucleic acids in which a 5-hydroxymethyl modification of the cytosine residue of interest is present, as well as nucleic acids in which a 5-methyl modification of said cytosine residue of interest is present and/or in which the cytosine residue of interest is not modified. In this manner, nucleic acids in which a 5-hydroxymethyl modification of the cytosine residue of interest is present are enriched in the mixture.

The enriched nucleic acids in which a 5-hydroxymethyl modification of the cytosine residue of interest is present, obtained according to the above two preferred embodiments of the method of the present invention, can be further used for any particular application of interest. For examples, said nucleic acids can be used for sequencing applications known in the art, including PCR and so-called Next Generation Sequencing methods, microarray analyses, or any methods for the analysis of 5-hydroxymethyl modified nucleic acids known in the art.

In a second aspect, the present invention relates to a method for the direct detection of a 5-hydroxymethyl modification of a cytosine residue of interest in a nucleic acid molecule, said method comprising the steps of:
(a) providing a transcription-activator-like effector (TALE) protein, said TALE protein being capable of binding in a sequence- and locus-specific manner to a region of said nucleic acid molecule that includes said cytosine residue of interest; and
(b) detecting a 5-hydroxymethyl modification of said cytosine residue of interest, wherein
  (i) said modification is present when said TALE protein does not bind to said region or does bind to said region with a strongly reduced affinity, and
  (ii) said modification is absent when said TALE protein binds to said region.

In preferred embodiments of the method of the present invention according to this second aspect, the repeat variable diresidue (RVD) of said TALE protein whose position corresponds to the position of the cytosine residue of interest is a sized reduced RVD. Preferably, size reduced RVDs comprise the RVDs H* and N*, wherein N* is particularly preferred.

In a third aspect, the present invention relates to a method for the enrichment of nucleic acid molecules in which a 5-hydroxymethyl modification of a cytosine residue of interest is present, said method comprising the steps of:
(a) providing a transcription-activator-like effector (TALE) protein, said TALE protein being capable of binding in a sequence- and locus-specific manner to a region of said nucleic acid molecule that includes said cytosine residue of interest, wherein the TALE protein is coupled directly or indirectly to an affinity ligand; and
(b) depleting nucleic acid molecules in which a 5-methyl modification of said cytosine residue of interest or said unmodified cytosine residue of interest is present via affinity chromatography using said affinity ligand.

In preferred embodiments of the method of the present invention according to this third aspect, the repeat variable diresidue (RVD) of said TALE protein whose position corresponds to the position of the cytosine residue of interest is a sized reduced RVD. Preferably, size reduced RVDs comprise the RVDs H* and N*, wherein N* is particularly preferred.

In a fourth aspect, the present invention relates to a method for the differential digestion of nucleic acid molecules in which a 5-methyl modification of a cytosine residue of interest or an unmodified cytosine residue of interest is present, wherein nucleic acid molecules in which a 5-hydroxymethyl modification of said cytosine residue of interest is present remain undigested, said method comprising the steps of:
(a) providing a transcription-activator-like effector (TALE) protein, said TALE protein being capable of binding in a sequence- and locus-specific manner to a region of said nucleic acid molecule that includes said cytosine residue of interest, wherein the TALE protein is coupled directly or indirectly to a protein having nuclease activity; and
(b) digesting nucleic acid molecules in which a 5-methyl modification of said cytosine residue of interest or said unmodified cytosine residue of interest is present using said protein having nuclease activity.

In preferred embodiments of the method of the present invention according to this fourth aspect, the repeat variable diresidue (RVD) of said TALE protein whose position corresponds to the position of the cytosine residue of interest is a sized reduced RVD. Preferably, size reduced RVDs comprise the RVDs H* and N*, wherein N* is particularly preferred.

All of the relevant definitions, explanations, and preferred embodiments defined above for the method according to the first aspect of the present invention expressly apply in an analogous manner also to the methods according to the second, third, and fourth aspect of the present invention.

In particular, in preferred and independent embodiments, (i) the nucleic acid molecule is preferably a DNA molecule, more preferably a double-stranded DNA molecule, (ii) the region to which said TALE protein is capable of binding in a sequence- and locus-specific manner is from 10 to 30 nucleotides in length, preferably from 12 to 28 nucleotides in length, more preferably from 14 to 24 nucleotides in length, (iii) said nucleic acid molecule is in its native state and is not chemically modified by any pretreatment, (iv) the affinity ligands include for example biotin, digoxigenin, dinitrophenol, magnetic particles, antibodies, including antibody fragments and antibody mimetics, and protein tags, and (v) the proteins having nuclease activity include for example restriction enzymes and cleavage domains of restriction enzymes, e.g. the cleavage domain of FokI.

In a fifth aspect, the present invention relates to the use of a transcription-activator-like effector (TALE) protein for the differentiation of a 5-hydroxymethyl modification of a cytosine residue of interest in a nucleic acid molecule from
(i) a 5-methyl modification of said cytosine residue of interest or
(ii) said unmodified cytosine residue of interest,
said TALE protein being capable of binding in a sequence- and locus-specific manner to a region of said nucleic acid molecule that includes said cytosine residue of interest.

In preferred embodiments of the use of the present invention according to this fifth aspect, the repeat variable diresidue (RVD) of said TALE protein whose position corresponds to the position of the cytosine residue of interest is a sized reduced RVD. Preferably, size reduced RVDs comprise the RVDs H* and N*, wherein N* is particularly preferred.

According to a preferred embodiment, this use is further for the direct detection of a 5-hydroxymethyl modification of said cytosine residue of interest in said nucleic acid molecule.

According to another preferred embodiment, this use is further for the enrichment of nucleic acid molecules in which a 5-hydroxymethyl modification of said cytosine residue of interest is present, wherein the TALE protein is coupled directly or indirectly to an affinity ligand.

According to yet another preferred embodiment, this use is further for the differential digestion of nucleic acid molecules in which a 5-methyl modification of said cytosine residue of interest or said unmodified cytosine residue of interest is present, wherein nucleic acid molecules in which a 5-hydroxymethyl modification of said cytosine residue of interest is present remain undigested, wherein the TALE protein is coupled directly or indirectly to a protein having nuclease activity.

In a sixth aspect, the present invention relates to the use of a transcription-activator-like effector (TALE) protein for the direct detection of a 5-hydroxymethyl modification of a cytosine residue of interest in a nucleic acid molecule, said TALE protein being capable of binding in a sequence- and locus-specific manner to a region of said nucleic acid molecule that includes said cytosine residue of interest.

In preferred embodiments of the use of the present invention according to this sixth aspect, the repeat variable diresidue (RVD) of said TALE protein whose position corresponds to the position of the cytosine residue of interest is a sized reduced RVD. Preferably, size reduced RVDs comprise the RVDs H* and N*, wherein N* is particularly preferred.

In a seventh aspect, the present invention relates to the use of a transcription-activator-like effector (TALE) protein for the enrichment of nucleic acid molecules in which a 5-hydroxymethyl modification of a cytosine residue of interest is present, said TALE protein being capable of binding in a sequence- and locus-specific manner to a region of said nucleic acid molecule that includes said cytosine residue of interest, wherein the TALE protein is coupled directly or indirectly to an affinity ligand.

In preferred embodiments of the use of the present invention according to this seventh aspect, the repeat variable diresidue (RVD) of said TALE protein whose position corresponds to the position of the cytosine residue of interest is a sized reduced RVD. Preferably, size reduced RVDs comprise the RVDs H* and N*, wherein N* is particularly preferred.

In an eighth aspect, the present invention relates to the use of a transcription-activator-like effector (TALE) protein for the differential digestion of nucleic acid molecules in which a 5-methyl modification of said cytosine residue of interest or said unmodified cytosine residue of interest is present, wherein nucleic acid molecules in which a 5-hydroxymethyl modification of said cytosine residue of interest is present remain undigested, said TALE protein being capable of binding in a sequence- and locus-specific manner to a region of said nucleic acid molecule that includes said cytosine residue of interest, wherein the TALE protein is coupled directly or indirectly to a protein having nuclease activity.

In preferred embodiments of the use of the present invention according to this eighth aspect, the repeat variable diresidue (RVD) of said TALE protein whose position corresponds to the position of the cytosine residue of interest is a sized reduced RVD. Preferably, size reduced RVDs comprise the RVDs H* and N*, wherein N* is particularly preferred.

All of the relevant definitions, explanations, and preferred embodiments defined above for the method according to the first aspect of the present invention expressly apply in an analogous manner also to the uses according to the fifth, sixth, seventh, and eighth aspect of the present invention.

In particular, in preferred and independent embodiments, (i) the nucleic acid molecule is preferably a DNA molecule, more preferably a double-stranded DNA molecule, (ii) the region to which said TALE protein is capable of binding in a sequence- and locus-specific manner is from 10 to 30 nucleotides in length, preferably from 12 to 28 nucleotides in length, more preferably from 14 to 24 nucleotides in length, (iii) said nucleic acid molecule is in its native state and is not chemically modified by any pretreatment, (iv) the affinity ligands include for example biotin, digoxigenin, dinitrophenol, magnetic particles, antibodies, including antibody fragments and antibody mimetics, and protein tags, and (v) the proteins having nuclease activity include for example restriction enzymes and cleavage domains of restriction enzymes, e.g. the cleavage domain of FokI.

Figure 2:
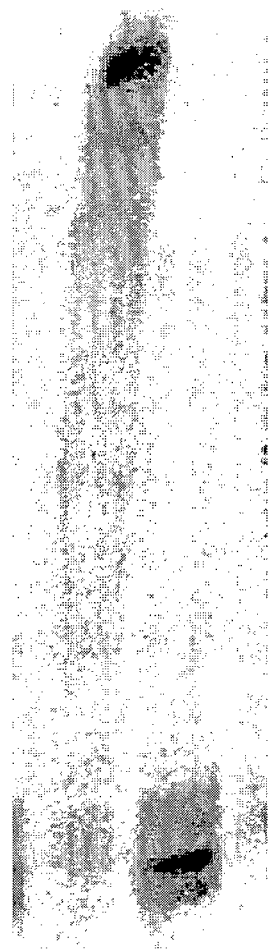

The present invention describes the sensitive discrimination of 5-hydroxymethyl modified cytosine residues over unmodified cytosine residues or 5-methyl modified cytosine residues in nucleic acid target sequences by binding of TALE proteins. Additionally, it has been discovered that the binding of TALE proteins effectively inhibits the activity of a DNA polymerase that binds the same site. In this way, the modification status of the target nucleic acid can be used to control DNA synthesis. This results in the possibility to link e.g. the sequence or concentration of a nucleic acid molecule that has been synthesized in a DNA polymerase-promoted primer extension to the cytosine modification status of the sample nucleic acid (cf. the scheme provided in FIG. 3). FIG. 2 shows a PAGE electrophoretic analysis of such a primer extension controlled by $^{5m}$C-dependent binding of a TALE protein.

Since there are numerous well-established methods to detect e.g. the sequence or concentration of specific nucleic acid molecules, the described TALE protein-based discrimination step can be directly integrated into various analytic methods such as PCR, qPCR, gel electrophoresis, array hybridization of obtained products, direct primer extensions on arrays using labeled dNTP, Sanger sequencing, Pyrosequencing and different approaches of Next- and Next-Next-Generation sequencing. This also includes sequence-by-synthesis, sequencing-by-ligation, single molecule sequencing in zero-mode waveguides and nanopore sequencing.

Additionally, the present invention provides very high flexibility and scope in respect to the target sequences. TALE proteins are highly modular and provide sufficient selectivity to be applicable in large, eukaryotic genomes. This strongly distinguishes them from previously employed, methylation-specific binding proteins. TALE proteins are additionally fully flexible in terms of target sequences and can be constructed and expressed with technical ease, providing the opportunity for high and ultra-high throughput approaches involving many TALE proteins in combination with one sample. Further, DNA polymerases are highly flexible in respect to the sequence of target nucleic acids that serve as primer/template complexes. Combined, this offers a very high potential of the present invention to be used in combination with various methods of nucleic acid sequence detection, various target sequences and different parallelization grades from single target assays to ultra-high throughput approaches.

Finally, the possibility to couple TALE proteins with a variety of compounds, proteins, affinity ligands, and other moieties allows for a wide range of applications for the detection, manipulation, purification, and analysis of 5-hydroxymethyl modified cytosine residues in nucleic acids.

The figures show:

FIG. 1:
Chemical structures of cytosine (C), 5-methylcytosine ($^{5m}$C) and 5-hydroxymethylcytosine ($^{5hm}$C).

FIG. 2:
PAGE analysis of a Primer Extension using a 5'-radiolabelled primer hybridized to a target DNA strand opposite a $^{5m}$C (left lane) or C (right lane). Primer template complexes were incubated with a TAL effector protein binding to the $^{5m}$C/C containing sequence and subsequently, a primer extension was conducted as shown in FIG. 3.

Figure 3:
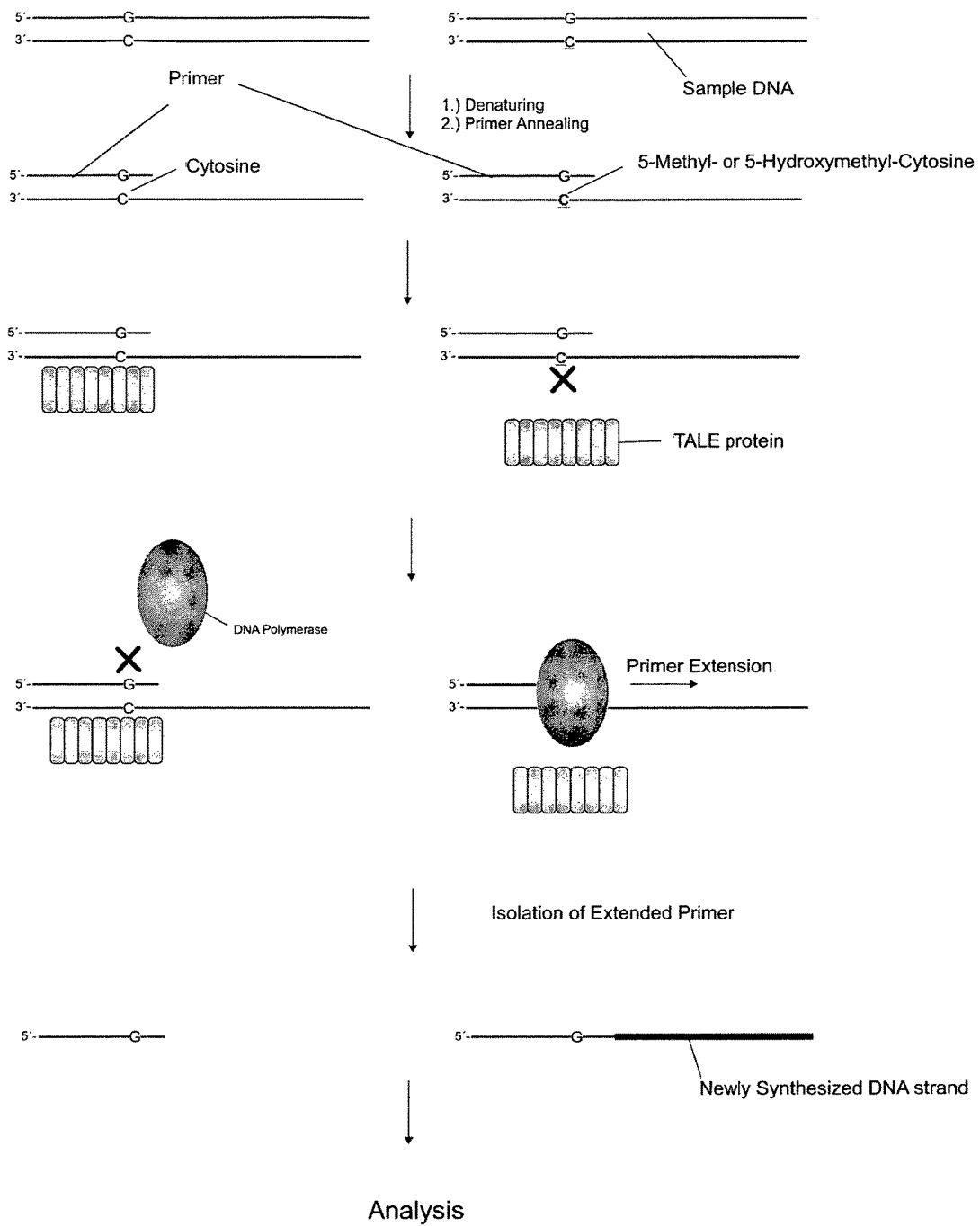

FIG. 3:
Principle and work flow of the method for detection of 5-modification status of C in dsDNA samples according to the present invention. Left: Binding of TALE to a primer-template complex containing a C opposite RVD HD inhibits primer extension by KF- (gray ellipse). Right: Presence of $^{5m}$C (shown as underlined C) prevents TALE-inhibition, leading to the synthesis of a DNA strand by KF- as signal (thick black bar in lower right part of the Figure).

Figure 4:
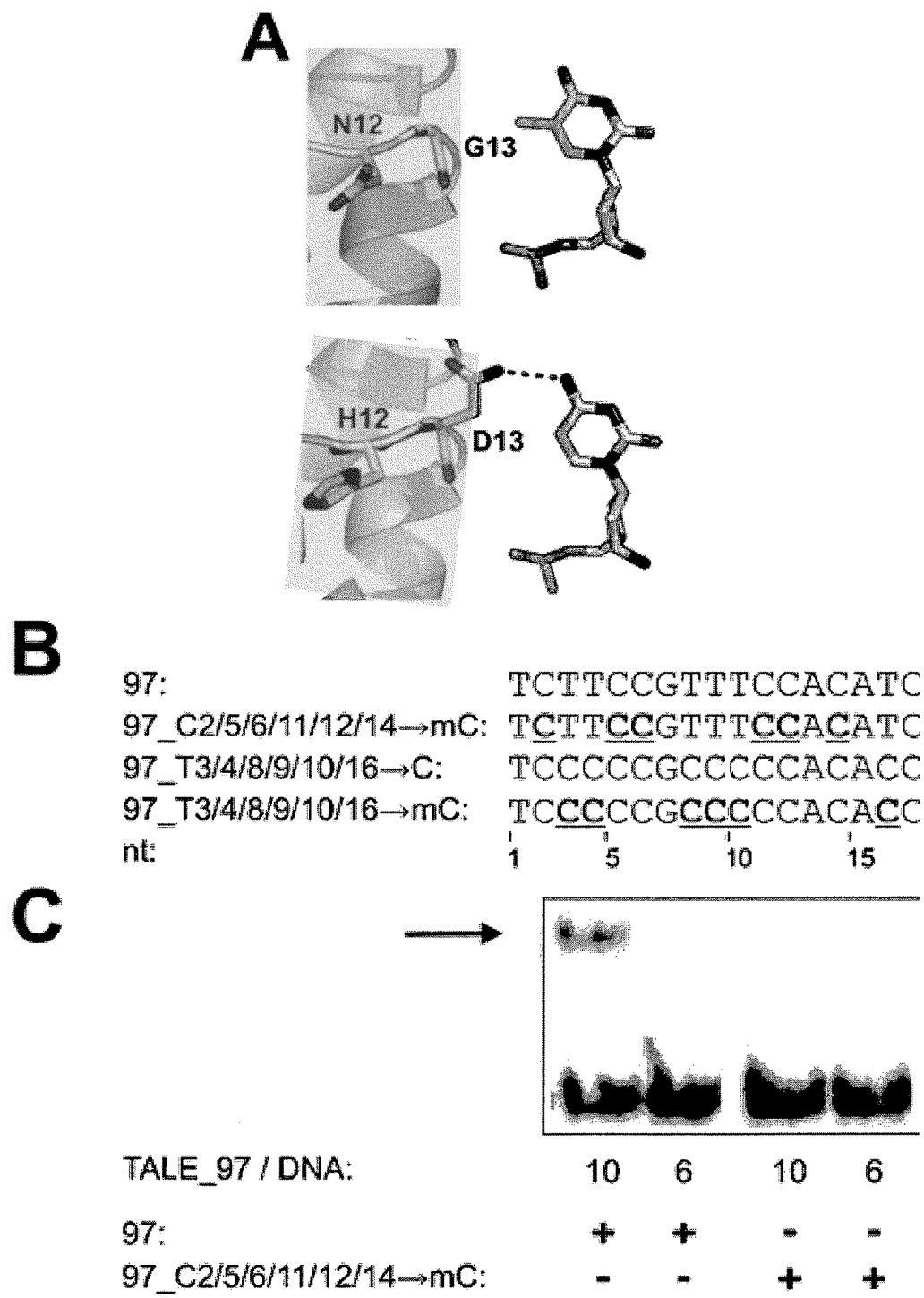

FIG. 4:
Recognition of thymine, C and $^{5m}$C in DNA by TALEs. A: Interaction of RVD NG (positions 12 and 13 of repeat) with thymine (top) and of RVD HD with C (bottom) in a crystal structure (pdb entry 3V6T). Hydrogen bond is shown as dotted line. B: Target DNA sequence 97 of TALE_97 and variants containing $^{5m}$C at six C positions and C or $^{5m}$C at six thymine positions of 97 (nt=nucleotide position, only forward strands are shown). C: EMSA assay using 5'-$^{32}$P-labelled DNA containing either C or $^{5m}$C as shown in B and TALE_97 with a TALE/target DNA ratio of 10 and 6, respectively. TALE-DNA complex is marked with an arrow.

Figure 5A:
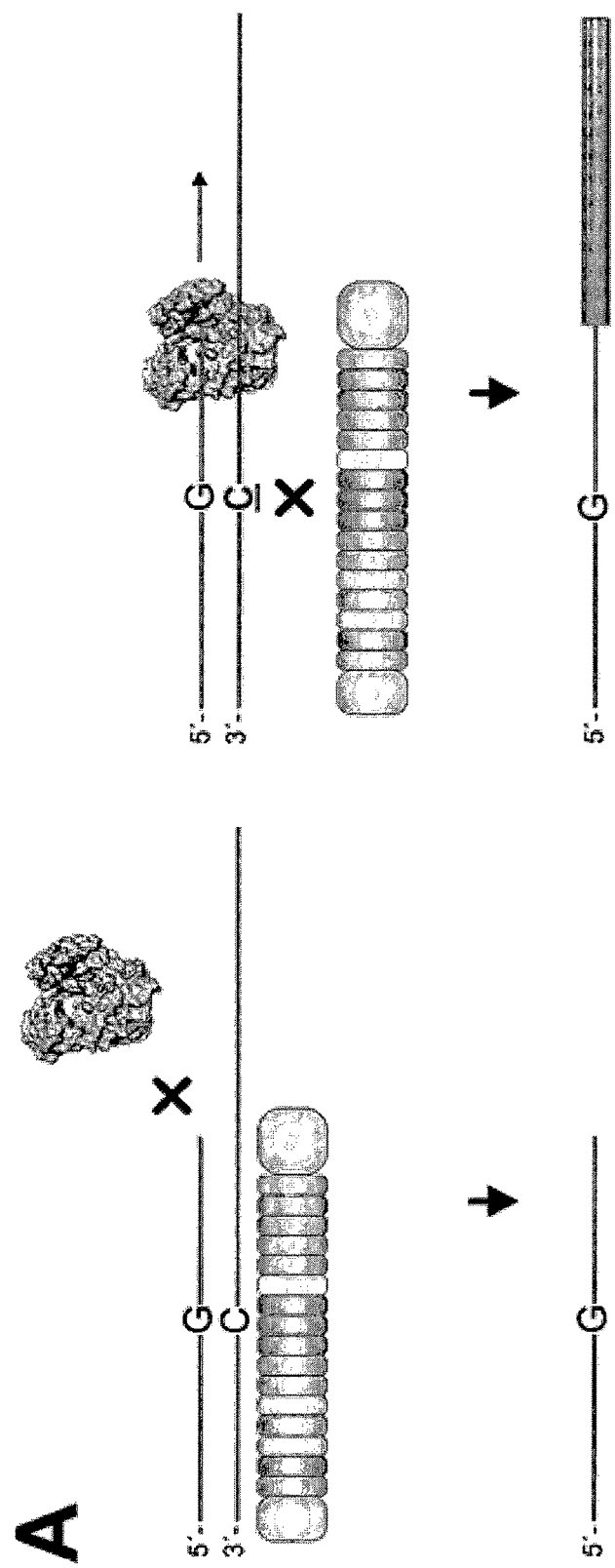

FIG. 5:
TALE-controlled DNA replication. FIG. 5A: General principle. Left: Binding of TALE to a primer-template complex containing a C opposite RVD HD inhibits primer extension by KF- (gray protein surface). Right: presence of $^{5m}$C (underlined) prevents TALE inhibition, leading to the synthesis of a DNA strand by KF- as signal (bar). FIG. 5B: Dependence of TALE-inhibition on the number and position of $^{5m}$C. PAGE analysis of primer extension reactions containing 0.125 U KF-, 8.325 nM primer-template complex with $^{5m}$C at indicated positions in presence or absence of 832.5 nM TALE_97. Primer and respective extension product are marked with a black and gray arrow, respectively. FIG. 5C: Sequence selectivity of TALE-inhibition. Experiments were conducted as in FIG. 5B using three different TALE proteins that target sequences present (TALE_97) or absent (TALE_57, _58) from the template strand.

Figure 6:
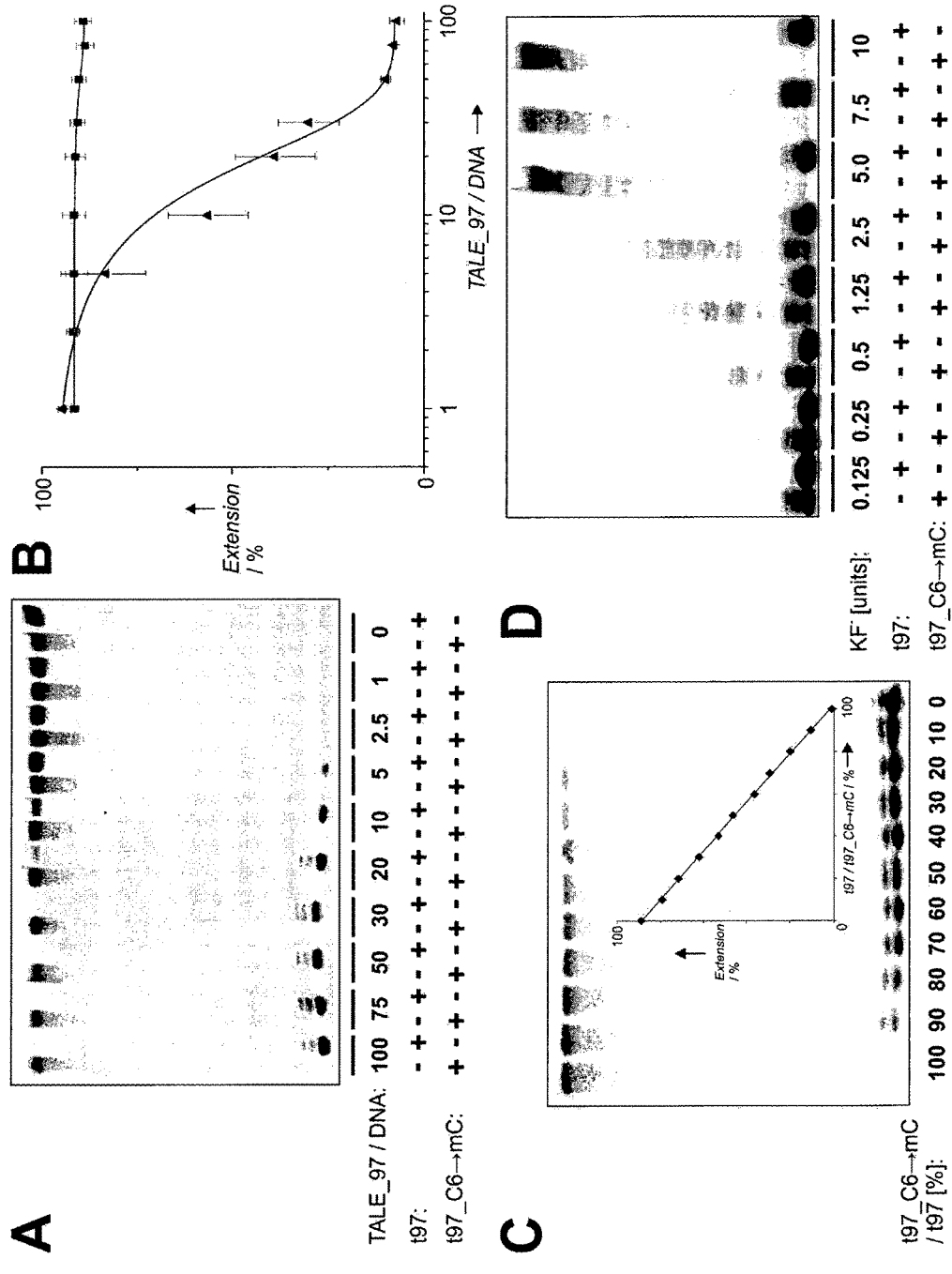

FIG. 6:
DNA replication inhibition by TALE, highly resolved detection of $^{5m}$C-modification level and influence of genomic DNA. A: Concentration dependence of KF--inhibition by TALE_97. Experiments were performed as in FIG. 5B with varying TALE_97/target DNA ratios and templates. B: Plot of primer extension product formation against TALE_97 concentration. Data for t97 and t97_C6 mC are shown as black triangles and gray squares, respectively. C: Dependence of TALE inhibition on $^{5m}$C modification level at a single nucleotide position. Experiments were performed as in FIG. 5B with mixes of t97 and t97_C6 mC. Inset shows linear regression of primer extension product formation plotted against t97/t97_C6 mC ratio in %. D: $^{5m}$C-discrimination in presence of excess gDNA. Experiments were performed as in FIG. 5B with 3×10⁴-fold mass excess of gDNA and varying amounts of KF-.

FIG. 7:

Primer extension experiments with maximized gDNA content. Experiments were carried out as in FIG. 6 panel D with reagent amounts as described in the figure. Upper Gel: Amount of salmon sperm genomic DNA in the reactions was varied between 0.1 and 10 μg/μL as shown in the figure. Lower Gel: Reaction was conducted as in FIG. 6 panel D with reagent amounts as described in the figure and with 10 μg/μL salmon sperm genomic DNA added to the reaction. Aliquots were removed at time points as shown in the figure (in hours) and analyzed by PAGE as shown.

FIG. 8:

Example reaction curves of qPCR analysis of $^{5m}$C-dependent primer extensions. Curve 1: t97_C6→mC (oGrK_465), ct 23.3; curve 2: t97 (oGrK_476), ct 29.7; curve 3: no template, ct 37.3.

FIG. 9:

SDS PAGE analysis of exemplary TALE expression and Ni-NTA-purification (pET_TRX_TAL1297_short). Lane 1: ladder; lane 2: pellet of expression culture, non-induced; lane 3: pellet of expression culture, induced with 1 mM IPTG; lane 4: combined wash fractions (buffer C); lane 5: combined elution fractions (buffer D); lane 6: combined elution fraction (buffer E).

FIG. 10:

qPCR concentration calibration with t97. $C_T$ values of calibration PCR reactions using t97 (oGrK_476, SEQ ID NO: 9) are shown as squares and of PCR reaction using agarose bead-immobilized primer extension products as circles, respectively.

FIG. 11:

PAGE analysis of a Primer Extension using a 5'-radiolabelled primer hybridized to a target DNA strand opposite a 5mC (lanes 2-8 and 10-14) at different positions within the target sequence or C (lane 1+9). All investigated positions show discrimination ability, with highest discrimination for C11, C13 and C14 and lowest discrimination for positions C17 and C8. Primer template complexes were incubated with a TAL effector protein binding to the 5mC/C containing sequence and subsequently, a primer extension was conducted as shown in FIG. 3.

FIG. 12:

PAGE analysis of a Primer Extension using a 5'-radiolabelled primer hybridized to a target DNA strand opposite a 5hmC (lane 1), 5mC (lane 2) or C (lane 3). TALEs discriminate between 5hmC and C as well. Primer template complexes were incubated with a TAL effector protein binding to the 5hmC/5mC/C containing sequence and subsequently, a primer extension was conducted as shown in FIG. 3.

FIG. 13:

PAGE analysis of a Primer Extension using a 5'-radiolabelled primer hybridized to a target DNA strand opposite a 5hmC (lanes 1, 4, 7, 10, 13, 16), 5mC (lanes 2, 5, 8, 11, 14, 17) or C (lanes 3, 6, 9, 12, 15, 18) after Incubation with TALE_97. Reducing KF amount reveals that discrimination for 5hmC is higher than for 5mC. Primer template complexes were incubated with a TAL effector protein binding to the 5hmC/5mC/C containing sequence and subsequently, a primer extension was conducted as shown in FIG. 3.

FIG. 14:

Diagram of primer extension inhibition by TALE_1297 containing RVDs N* or NG at position 5, binding to their target sequence bearing a C, mC or hmC opposite the RVD of position 5. Top: PAGE analysis. Bottom: Same experiment with mixture of DNAs containing the target sequence bearing a C, mC or hmC opposite the RVD of position 5. Mixture is indicated under the graphs, named modification level in %. X-axis: % extension product, i.e. Phosphorimager signals of individual lanes of PAGE gels for full-length primer extension product divided through full signal of the lane in %.

FIG. 15:

FIG. 15A: Top: Table of Ki values for TALE_1297 containing RVDs HD, N* or NG at position 5, binding to their target sequence bearing a C, mC or hmC opposite the RVD of position 5. Bottom: Diagram of primer extension inhibition by TALES as above with target DNA used above at constant TALE-DNA ratios. X-axis: Extension Product. FIG. 15E; KI-graph for TALE 1297 containing RVD HD at position 5. FIG. 15C: KI-graph for TALE 1297 containing RVD N* at position 5. FIG. 15D: KI-graph for TALE 1297 containing RVD NG at position 5.

FIG. 16:

Current model for the complete cycle of dynamic cytosine modification as central mechanism for the regulation of gene expression. TET: ten-eleven translocation dioxygenase. TDG: thymine DNA glycosylase. BER: base excision repair.

The present invention will now be further illustrated in the following examples without being limited thereto.

EXAMPLES

Experimental Procedures

Construction of TALE Expression Plasmids.

Fragments containing the N- and C-terminal sequences of a *Xanthomonas axonopodis pathovar citri* TALE with variable numbers of internal repeats were amplified from plasmids TALEN1297, TALEN1257 and TALEN1258 (Addgene plasmids 32279, 32280, 32281) with primers oDaS308 (dHax_hom_KpnI_fwd, SEQ ID NO: 1) and oDaS231 (dHax_hom_NotI_His6_rev, SEQ ID NO: 2) and cloned into the KpnI and EagI sites of plasmid pET32a-TRX (Addgene plasmid 11516). This resulted in plasmids pET_TRX_TAL1257_short, pET_TRX_TAL1258_short and pET_TRX_TAL1297_short coding for the respective TALE proteins with N-terminal thioredoxin (TRX) tag and S-tag, and a C-terminal His6 tag.

Expression and Purification of TALE Proteins.

Figure 9:
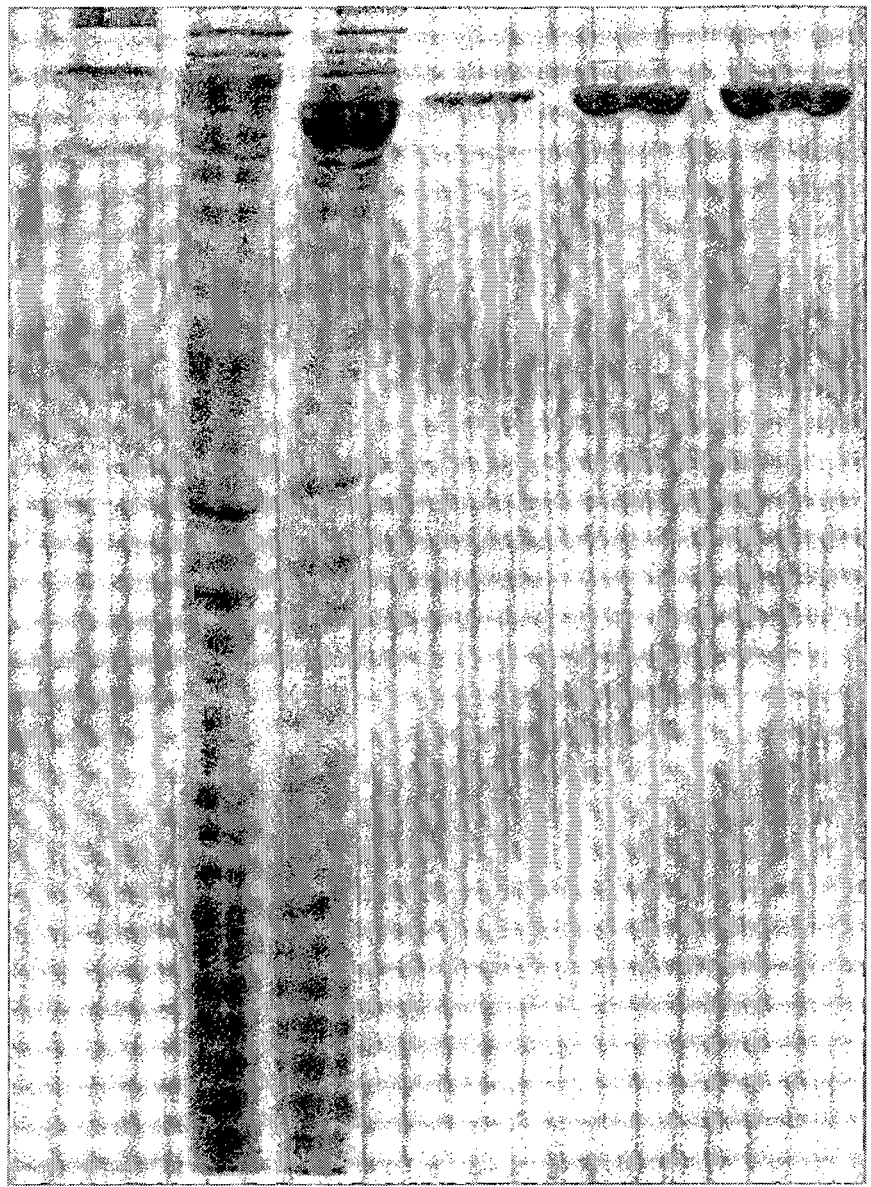

*E. coli* BL21(DE3) Gold was transformed with pET_TRX_TAL1257_short, pET_TRX_TAL1258_short or pET_TRX_TAL1297_short and a single clone was picked and was grown overnight in Luria Broth (LB) media supplemented with 50 g/ml carbenicillin at 37° C. and 200 rpm shaking. This culture was diluted 50-fold into LB medium supplemented with 50 g/ml carbenicillin and the culture was incubated at 37° C. and 200 rpm shaking until an OD600 of ~0.6 was reached. Protein expression was induced with 1 mM IPTG and the culture was harvested after 3 h of incubation by centrifugation (10 min, 3320×g, room temperature). The pellet was lysed with B-Per lysis reagent (Thermo Scientific) containing 1× complete (-EDTA) protease inhibitors (Roche) and shaking at room temperature at 1400 rpm for 20 min. The suspension was pelleted by centrifugation (5 min, 20817×g, room temperature) and the supernatant was discarded. Protein was extracted from pellet under denaturing conditions and bound to Ni-NTA (Qiagen) according to the manufacturer's protocol. Ni-NTA was washed 2 times with 500 μl Buffer C (Qiagen) and eluted with buffer D (Qiagen) and then 3 times with buffer E (Qiagen). Pooled elution fractions were added to a Slide-A-Lyzer dialysis tube (Thermo Scientific) and dialyzed against TALE Storage Buffer (20 mM Tris-HCl pH=7.5, 200 mM NaCl, 10% Glycerol, 1 mM DTT). Purity and quantity of TALE proteins was analyzed by SDS PAGE and staining with Gelcode blue (Thermo Scientific) (FIG. 9) and a BCA assay (Pierce) and proteins were stored in aliquots at −80° C. in TALE storage buffer including 0.1 mg/ml bovine serum albumin (BSA, New England Biolabs).

Electromobility Shift Assays.

Oligonucleotides 97_C2/5/6/11/12/14 mC_rev (SEQ ID NO: 5) and 97_T3/4/8/9/10/16 mC_rev (SEQ ID NO: 8) were 5'-$^{32}$P-end labeled using γ-$^{32}$P-ATP and T4 polynucleotide kinase (Fermentas) and purified using a G-25 gel filtration column (GE Healthcare). Oligonucleotides were hybridized pairwise (97/97_C2/5/6/11/12/14 mC_rev (SEQ ID NO: 3/SEQ ID NO: 5); 97_C2/5/6/11/12/14 mC/97_C2/5/6/11/12/14 mC_rev (SEQ ID NO: 4/SEQ ID NO: 5); 97_T3/4/8/9/10/16 C/97_T3/4/8/9/10/16 mC_rev (SEQ ID NO: 6/SEQ ID NO: 8); 97_T3/4/8/9/10/16 mC/97_T3/4/8/9/10/16 mC_rev (SEQ ID NO: 7/SEQ ID NO: 8)) at a concentration of 12.5 nM, respectively, by incubating at 95° C. for 5 min and subsequently at room temperature for 30 min in Hybridization buffer (40 mM Tris-HCl (pH=8.0), 100 mM NaCl, 10 mM $MgCl_2$, 100 ng/µl salmon sperm DNA (Ambion), 0.2 mg/ml BSA, 10% glycerol). For TALE-binding, to 6 µL of the hybridized DNA duplexes, 6 µL of TALE storage buffer (20 mM Tris-HCl pH=7.5, 200 mM NaCl, 10% Glycerol, 1 mM DTT) with varying concentrations of TALE proteins were added and mixtures were incubated at room temperature for 30 min. Mixtures were loaded onto an analytical, non-denaturing PAGE-gel (0.5 mm, 50 cm length) that was run in 0.25×TB buffer at 12 W and room temperature. Gel was dried and data recorded on a phosphorimager.

Primer Extension Reactions.

Templates as shown in FIG. 2 (SEQ ID NOs: 9 to 14) and primer p97_rev (SEQ ID NO: 15; 5'-$^{32}$P-end labeled as above) were diluted from 5× stocks (500 nM and 166.5 nM, respectively) into 6 µL Hybridization buffer (40 mM Tris-HCl (pH 8.0), 100 mM NaCl, 10 mM $MgCl_2$, 0.2 mg/ml BSA, 10% glycerol) to final concentrations of 100 nM and 33.3 nM and hybridized by incubating at 95° C. for 5 min and subsequently at room temperature for 30 min. TALE proteins with various RVDs at position 5 were added in 6 µl TALE storage buffer (200 mM NaCl, 20 mM Tris-HCl (pH 7.5), 1 mM DTT, 10% glycerol) at varying concentrations and mixtures were incubated at room temperature for 30 min. 12 µl of a mixture of 25 mU Klenow Fragment of E coil DNA polymerase (3'-5'-exo$^-$, New England Biolabs) and 200 µM of each dNTP in Binding buffer (30 mM Tris-HCl (pH 8.0), 150 mM NaCl, 5 mM $MgCl_2$, 0.1 mg/ml BSA, 0.5 mM DTT, 7.5% glycerol) were added, resulting in final concentrations of 8.325 nM and 25 nM for primer and template, respectively. These mixtures were incubated at room temperature for additional 15 min. 12 µl of PAGE loading buffer (80% formamide, 2 mM EDTA) were added, the mixtures were incubated at 95° C. for 5 min and cooled to 4° C. Mixtures were loaded onto a pre-run, analytical denaturing PAGE ad (9 M urea, 0.5 mm, 50 cm length) and gel was run in 1×TBE at 120 W and 40-50° C. Gel was dried and data recorded on a phosphorimager. For $IC_{50}$ determination (FIG. 6 panel B), fitting was performed in Origin 8.6.0G (Originlab) using the Dose Response function without initial parameters or by linear regression in MS Excel.

To investigate the influence of additional genomic DNA (gDNA), the hybridization of templates and primer p97_rev were conducted as above using Hybridization buffer containing 0.1-10 µg/µl salmon sperm DNA in a 6 µl total volume. This corresponds to a mass ratio of $2.89 \times 10^2$-$2.89 \times 10^4$, calculated with the molecular weight of double stranded target sequence 97 (10379.9 g/mol, FIG. 4B, SEQ ID NO: 3). 6 µl of a 1.665 µM TALE_97 solution in TALE storage buffer were added resulting in a TALE/target DNA ratio of 50:1. Mixtures were incubated at room temperature for 30 min. 12 µL of Binding buffer containing 0.125 to 10.0 U Klenow Fragment of E. coli DNA polymerase I (3'-5'-exo-, New England Biolabs) and 200 µM of each dNTP were added and the resulting mixtures were incubated at room temperature for additional 15 to 720 min. 12 µL of PAGE loading buffer were added, the mixtures were incubated at 95° C. for 5 min and cooled to 4° C. Mixtures were loaded onto a pre-run, analytical denaturing PAGE gel (9 M urea, 0.5 mm, 50 cm length) and gel was run in 1×TBE at 120 W and 40-50° C. Gel was dried and data recorded on a phosphorimager.

qPCR Experiments.

Figure 10:
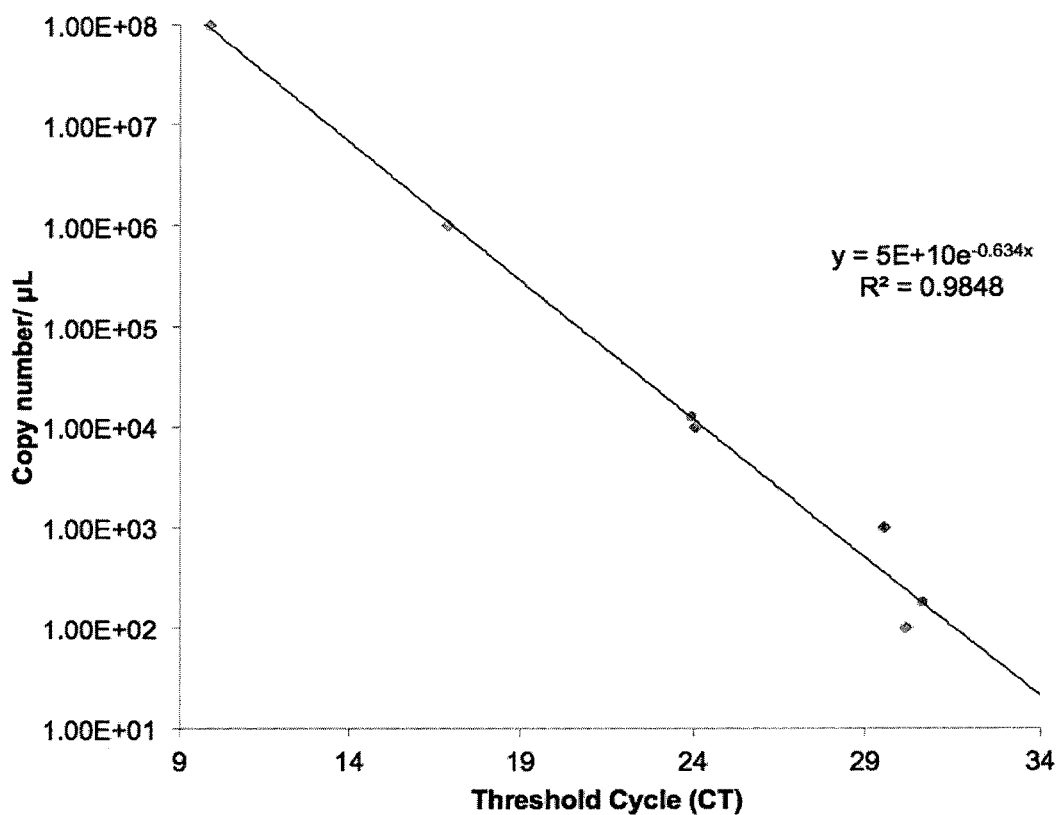

For qPCR experiments, primer extension reactions were conducted as above with primer Bio-p97_rev (SEQ ID NO: 15) replacing 5'-32P-radiolabelled primer p97_rev. Reactions were quenched with 12 µL of 20 mM EDTA. Mixtures were diluted with water to 500 µL and 10 µL of streptavidin-agarose beads (Sigma-Aldrich, pre-incubated 4 h in 20 mM NaOH) were added. Suspensions were shaken for 30 min and agarose beads were washed 4 times with 20 mM NaOH, 2 times with water and 2 times with PBS buffer (each 100 µL). To not introduce bias into copy numbers of primer extension products, streptavidin agarose was used in a 400-fold excess of biotin binding sites over molecules of added primer. For PCR reactions, agarose beads were diluted in PBS to contain $1/10^5$ of above primer extension reactions in 10 µL of bead suspension. PCR reactions (50 µL) were conducted with using 25 µL GoTaq qPCR Master Mix containing BRYT Green dye, 200 nM of each primer qp97_fwd (oGrK_621, SEQ ID NO: 16) and primer qp97_rev (oGrK_622, SEQ ID NO: 17) and 10 µL of above diluted bead suspension in a BioRad i-Cycler with filters FAM-490 using the following program: 2 min 95° C., then 60 cycles of 0:15 min 95° C., 1:00 min 60° C. Reproduction experiment to obtain standard deviations of CT values included the complete experimental procedure starting from primer extension reactions. For quantification of copy numbers present in agarose bead PCR reactions, a calibration curve was generated using the same PCR conditions and dilutions of t97 (oGrK_476) (FIG. 10). Copy numbers were obtained by linear regression. PCR products were additionally analyzed by agarose gel electrophoresis and staining with ethidium bromide.

Example 1

It was aimed to get deeper insights into the binding of TALE proteins to C and $^{5m}$C and to exploit it for the development of a methodology for programmable, locus-specific $^{5m}$C-detection. TALE_97 was designed and expressed, a construct targeting a 17 nt sequence of the zebrafish (*Danio rerio*) hey2 gene derived from a natural TALE scaffold from *Xanthomonas axonopodis*. To evaluate the general discrimination ability of TALE_97, its binding to DNA containing its target sequence ("97", FIG. 4B) with either C or $^{5m}$C at six scattered positions opposite six NG or HD RVDs was analyzed in electromobility shift assays (EMSA, FIG. 4C).

No difference in binding was observed when either C- or $^{5m}$C-containing nucleotides were placed opposite NG RVDs (data not shown). In contrast, for HD RVDs, binding was observed for DNA containing C, but not for DNA containing $^{5m}$C (FIG. 4C).

Example 2

Next it was investigated whether the discrimination found in Example 1 could be exploited for sensitive and highly resolved $^{5m}$C-detection. For that purpose, it was aimed to couple TALE-binding to DNA replication by DNA polymerase. Newly synthesized DNA molecules with defined sequence could then provide a signal for $^{5m}$C-modification that can be quantitatively detected by selective and sensitive analysis techniques.

Though TALEs and DNA polymerases generally recognize DNA differently, i.e. through the opposing major and minor grooves, they directly and indirectly compete for phosphate- and nucleobase-interactions, and induce differential conformations in bound DNA. TALEs could thus indeed be able to control DNA polymerase-catalyzed DNA synthesis by inhibitive binding (FIG. 5A).

A 79 nt DNA oligonucleotide template consisting of a region of the hey2 gene with sequence 97 (FIG. 4B) at the 3'-terminus (t97) was hybridized with a reverse complement, 5'-32P-labelled primer (p97_rev) and the complex incubated with or without 100 equivalents of TALE_97. Then dNTP and the Klenow fragment of E. coli DNA polymerase I (3'-5'-exo-, KF-) was added, the mixture incubated and subsequently resolved by denaturing polyacrylamide gel electrophoresis (PAGE). Primer extension was observed when TALE_97 was absent, but was completely abolished in its presence (FIG. 5B, lanes 1-2), indicating that this protein is indeed an effective inhibitor of KF--catalyzed DNA synthesis.

Example 3

Next it was investigated if this inhibition potential of TALE_97 could be combined with its observed discrimination of multiple $^{5m}$C-positions opposite HD RVDs (FIG. 4C) to enable $^{5m}$C-dependent DNA synthesis. To test if the resolution of $^{5m}$C-detection could be enhanced compared to the one observed in EMSA, a primer extension reaction was performed as above with a template that contained only three instead of six $^{5m}$C at the positions 2, 6 and 14 (t97_C2/6/14 mC). No inhibition of primer extension was observed (FIG. 5B, lane 3), indicating that TALE_97 provides higher $^{5m}$C-discrimination ability than observed before. To test if this resolution could be increased even further, reactions were performed using templates containing only two or one $^{5m}$C at different positions (t97_C2/6 mC, t97_C2 mC, t97_C6 mC, t97_C14 mC; FIG. 5B, lanes 4-7). TALE_97 was able to discriminate $^{5m}$C in all cases. However, when testing t97_C14 mC having an mC position close to the C-terminus, reduced primer extension was observed, indicating that a certain degree of TALE-binding was occurring, despite the presence of $^{5m}$C at position 14. This suggests that there are no strict constraints regarding the repeat position used for discrimination, but that repeats in the middle and N-terminal region may have superior discrimination ability than repeats in the C-terminal region.

Example 4

To be useful for locus-specific $^{5m}$C-detection, the observed $^{5m}$C-dependent inhibition of KF- by TALEs has to be strictly sequence-selective under conditions that are compatible with KF--catalyzed DNA synthesis. Two additional TALEs based on the identical scaffold as used for TALE 97 were constructed and expressed (TALE_57 and _58). These recognize sequences in the hey2 gene adjacent to sequence 97 and in the gria3a gene of zebrafish, respectively, that are both absent from t97. Primer extension reactions were performed using templates t97 and t97_C6 mC in presence of either TALE_97, 57, or _58 (FIG. 5C). TALE_97 still effectively discriminated against the single $^{5m}$C position (FIG. 5C, lanes 1-2), and the presence of either TALE_57 or _58 did not reduce primer extension, regardless of the presence of C or $^{5m}$C in the template (FIG. 5C, lanes 3-6). This indicates that inhibition of KF- by TALEs is indeed sequence-selective.

Example 5

To gain quantitative insights into the $^{5m}$C-discrimination ability of TALE_97, primer extension reactions were performed with templates t97 and t97_C6 mC with varying TALE_97/target DNA ratios (FIG. 6 panel A).

For t97, primer extension declined with increasing TALE concentrations. Inhibition was visible from a ratio of 5 and was virtually complete at an optimum ratio of 50 ($IC_{50}$=106.4±11 nM, FIG. 6 panel B), In contrast, no effect was observed for t97_C6 mC even at the highest ratio, confirming highly effective discrimination.

Example 6

DNA-associated, $^{5m}$C-dependent processes are not only controlled by the status but also by the level of $^{5m}$C-modification. An ideal $^{5m}$C-detection method should thus allow analysis of this parameter. Primer extension reactions were performed with TALE_97 and mixed t97 and t97_C6 mC templates, resulting in $^{5m}$C-modification levels between 0 and 100% in increments of 10% (FIG. 6 panel C). Over the complete range, the dependence of primer extension product formation on the $^{5m}$C-modification level of the single analyzed nucleotide position was strictly linear (FIG. 6 panel C). This offers highly resolved, quantitative analysis.

Example 7

For direct application to biological samples without target sequence enrichment, an $^{5m}$C-detection method should offer high robustness towards the presence of excess genomic DNA (gDNA). Primer extension reactions were performed as above in presence of salmon sperm gDNA (up to a viscosity limit of a $3 \times 10^4$-fold mass excess over primer) during the hybridization step. Above $3 \times 10^2$, no full-length primer extension product was obtained (FIG. 7), suggesting masking of KF-activity. We repeated the experiment with a $3 \times 10^4$-fold excess of gDNA and increasing amounts of KF- (FIG. 6 panel D). From an amount of 5 units per reaction, both primer extension and high $^{5m}$C-discrimination were fully restored (a similar result was obtained by increasing the primer extension time, FIG. 7). This high robustness towards the presence of gDNA offers promising perspectives for a direct application with complex biological samples.

Example 8

Figure 8:
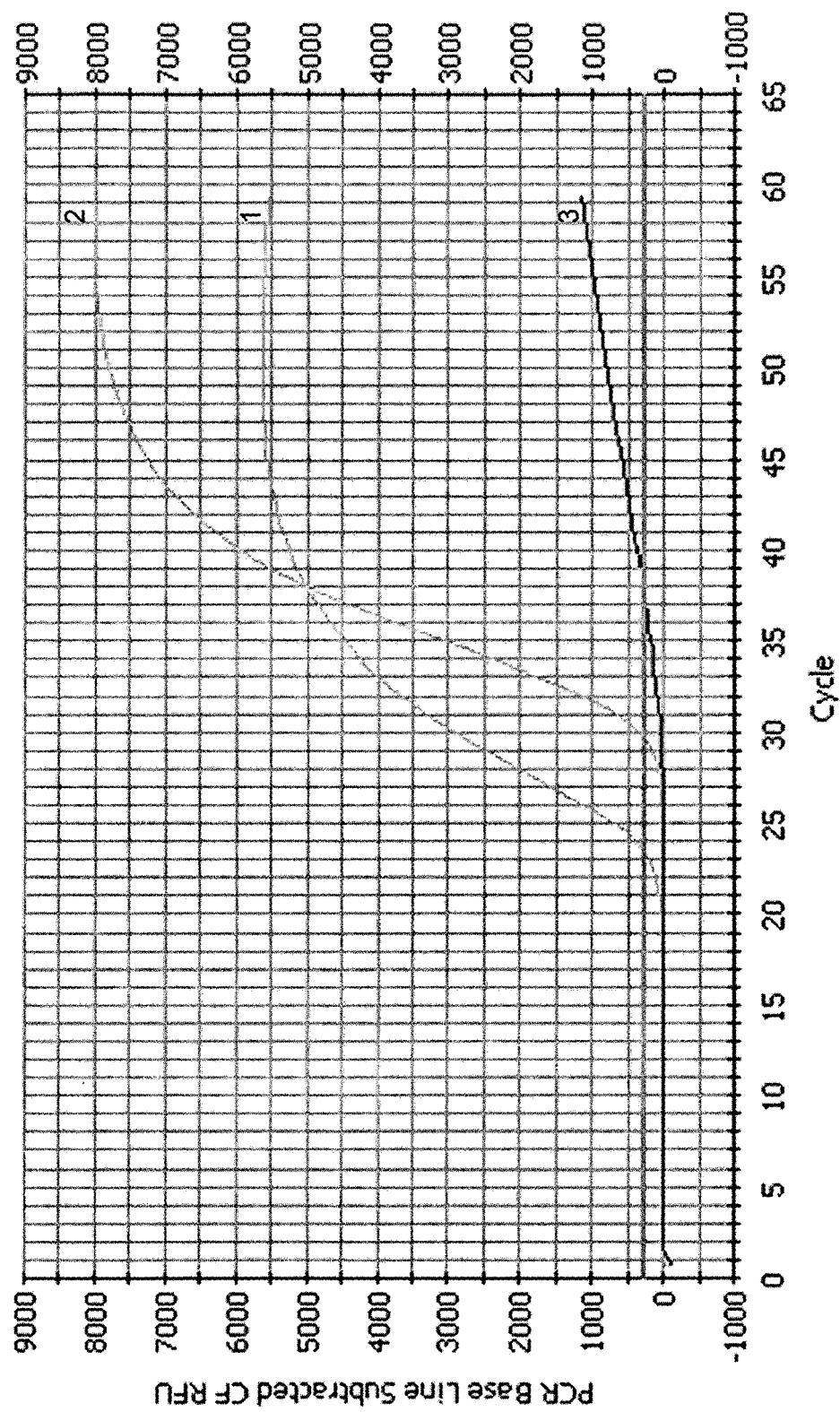

To test, if the chosen signaling strategy would provide high sensitivity, it was aimed to read out primer extension products by qPCR. Reactions with templates t97 and t97_C6 mC were repeated as above using a 5'-biotin labeled primer (Bio-p97_rev). Subsequently, the reactions were incubated with an excess of streptavidin-agarose beads and non-biotinylated template removed by extensive washing with 20 mM NaOH. Then, $1/10^5$ of the beads were used in a qPCR experiment using generic fluorescence signaling with primers targeting the hey2 sequence that was expected to be present in the primer extension products. For reactions conducted with t97_C6 mC and t97, fluorescence threshold cycles (CT) of 23.9±0.9 and CT of 30.7±1.3 were obtained, respectively (FIG. 8). This corresponds to a 71-fold difference in template copy number. For comparison, a 78-fold difference in full-length primer extension product was obtained by PAGE and phosphorimager quantification as above. This shows that the mC-discrimination by TALE_97 in primer extensions can be quantitatively reflected by qPCR, which offers to significantly increase the sensitivity of the method.

Example 9

Figure 11:
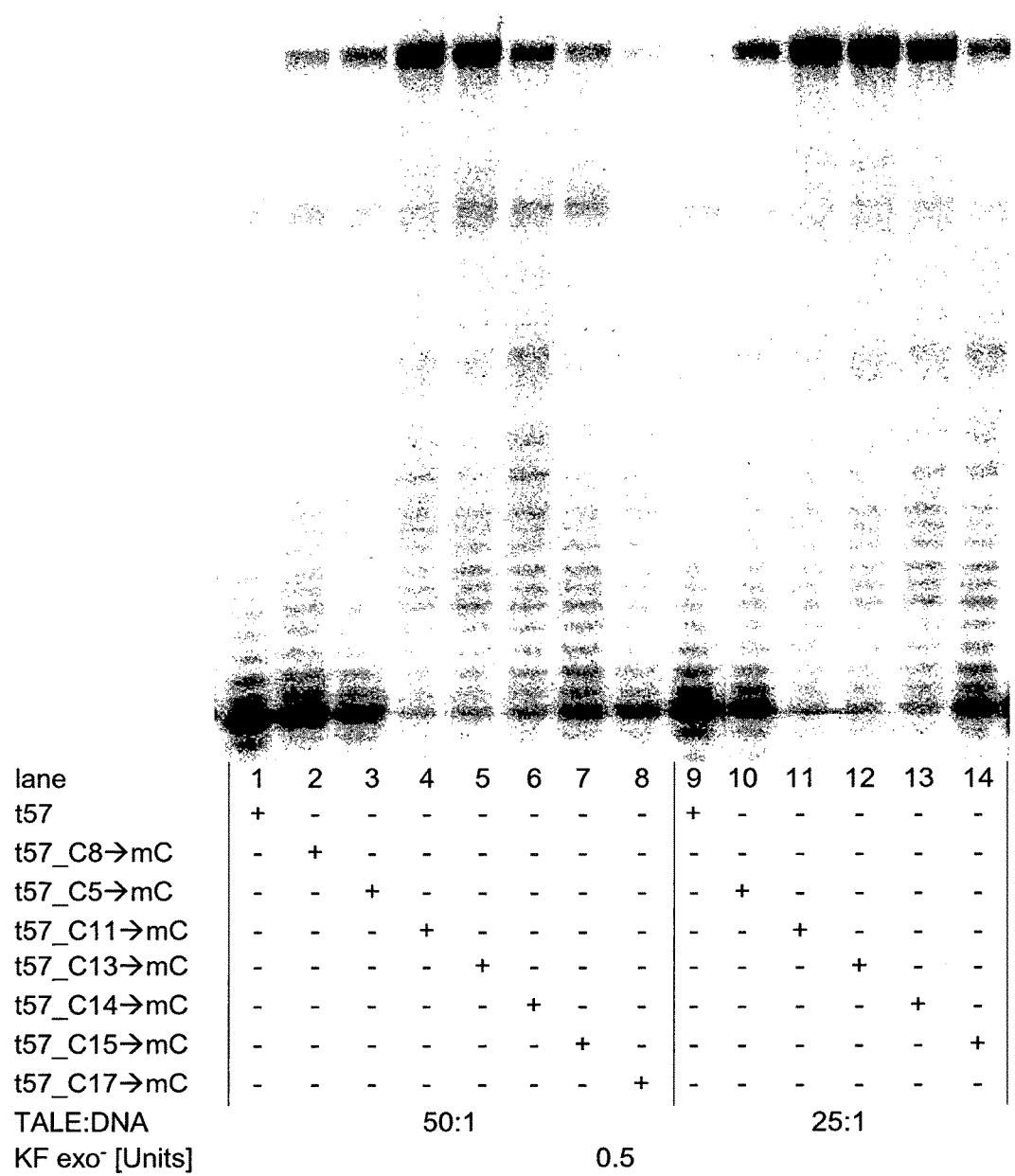

Next, the position-dependence of discrimination was further analyzed using TALE_57 under primer extension conditions as used in the experiments of FIG. 5B. Primer extension reactions were conducted with a TALE:target DNA ratio of 50:1 and 25:1. Discrimination was observed in all cases (FIG. 11).

Example 10

Figure 12:
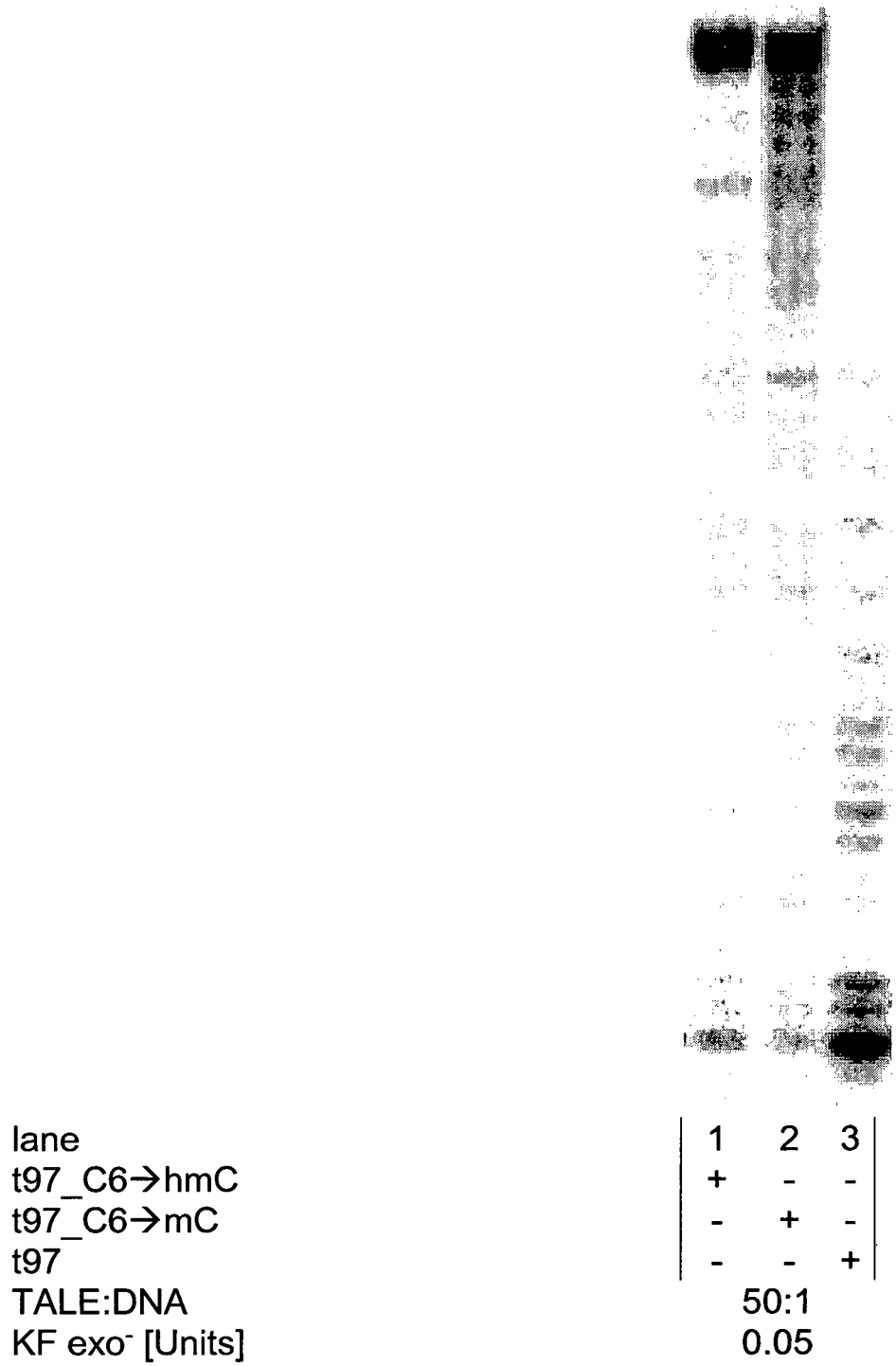
Figure 13:
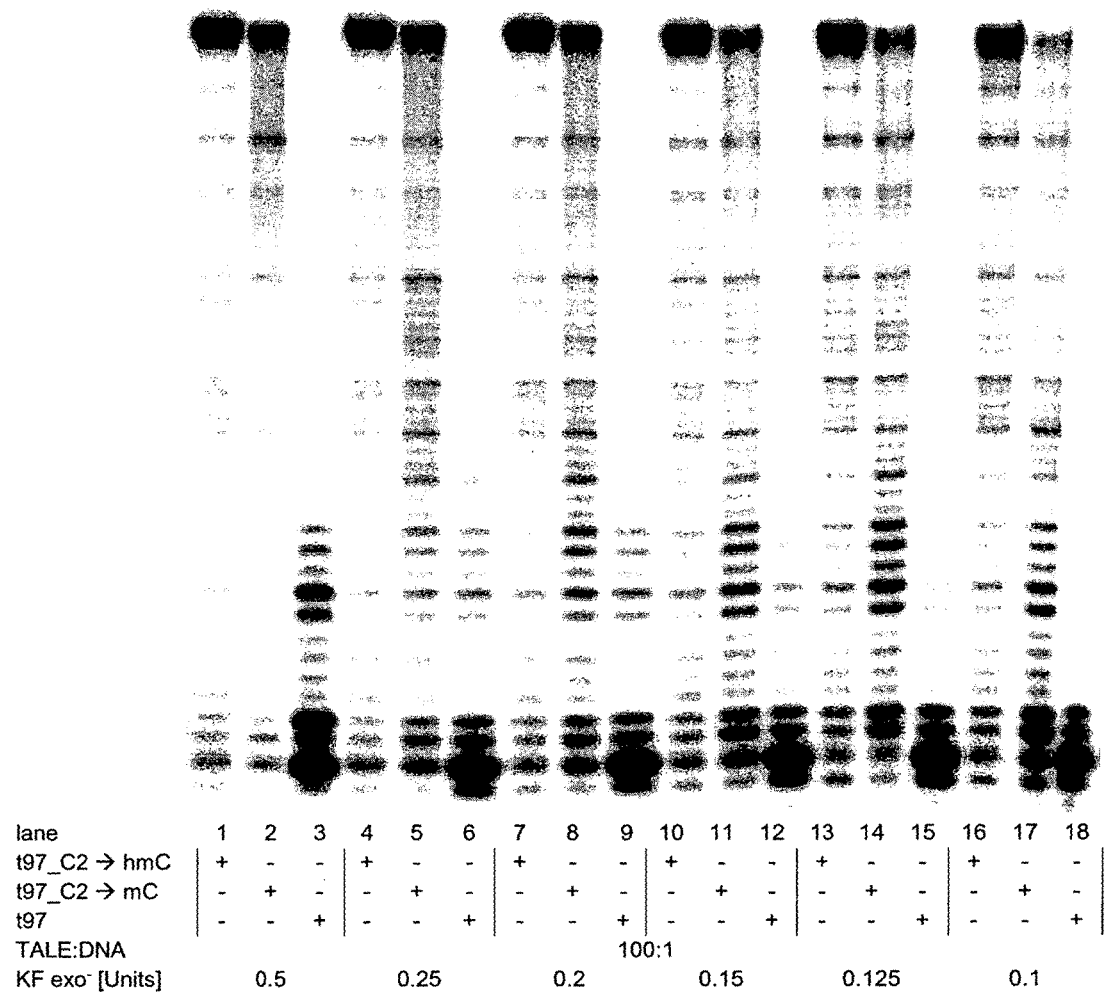

Next, discrimination of the epigenetic cytosine modification 5-hydroxymethylcytosine ($^{5hm}C$) by TALE_97 was tested and compared with the discrimination of $^{5m}C$. Primer extension reactions were conducted as in the experiments shown in FIG. 5B with a TALE:target DNA ratio of 50:1. These experiments show that $^{5hm}C$ can also be discriminated by the approach (FIG. 12). To assess if the discrimination ability of TALE_97 was different for $^{5m}C$ and $^{5hm}C$, primer extension reactions under conditions as for the experiments shown in FIG. 5B were conducted with a TALE:target DNA ratio of 100:1 and varying amounts of KF-. These experiments revealed a stronger discrimination for $^{5hm}C$ than for $^{5m}C$ (FIG. 13).

Example 11

Figure 14:
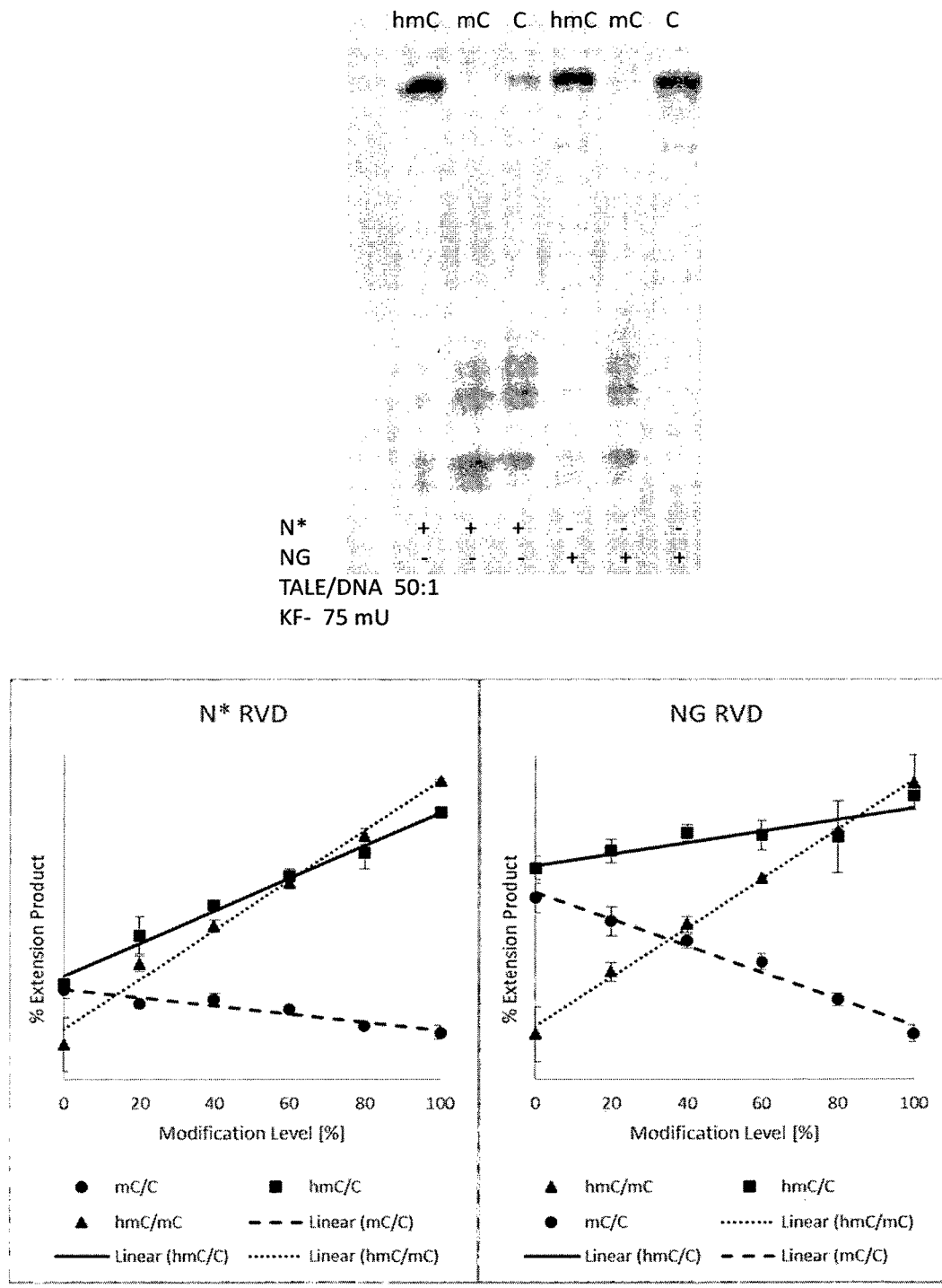

Next it was investigated if the slight discrimination ability of TALE_97 between $^{5hm}C$ and $^{5m}C$ could be improved by placing less sterically demanding RVDs opposite the investigated C. TALE_037 and TALE_038 were assembled providing RVD N* or NG respectively opposite of C6 in the target sequence. Primer extension reactions were performed as above with a TALE:target DNA ratio of 50:1 with templates containing $^{5hm}C$, $^{5m}C$ or C at position 6. In case of NG RVD limited inhibition of primer extension was observed for $^{5hm}C$ modified and unmodified DNA and stronger inhibition for DNA containing $^{5m}C$ at position 6, indicating that TALE_038 provides ability for discrimination of $^{5hm}C/C$ and $^{5m}C$ (FIG. 14 lanes 4-6). This could be already used for sequence specific determination of $^{5hm}C$ by comparison to primer extension results using TALE_97. In case of N* RVD no inhibition of primer extension was observed for $^{5hm}C$ modified DNA and strong inhibition for DNA containing $^{5m}C$ and C at position 6, indicating that TALE_037 provides high ability for discrimination of $^{5hm}C$ and $^{5m}C/C$ (FIG. 14 lanes 1-3).

Figure 15:
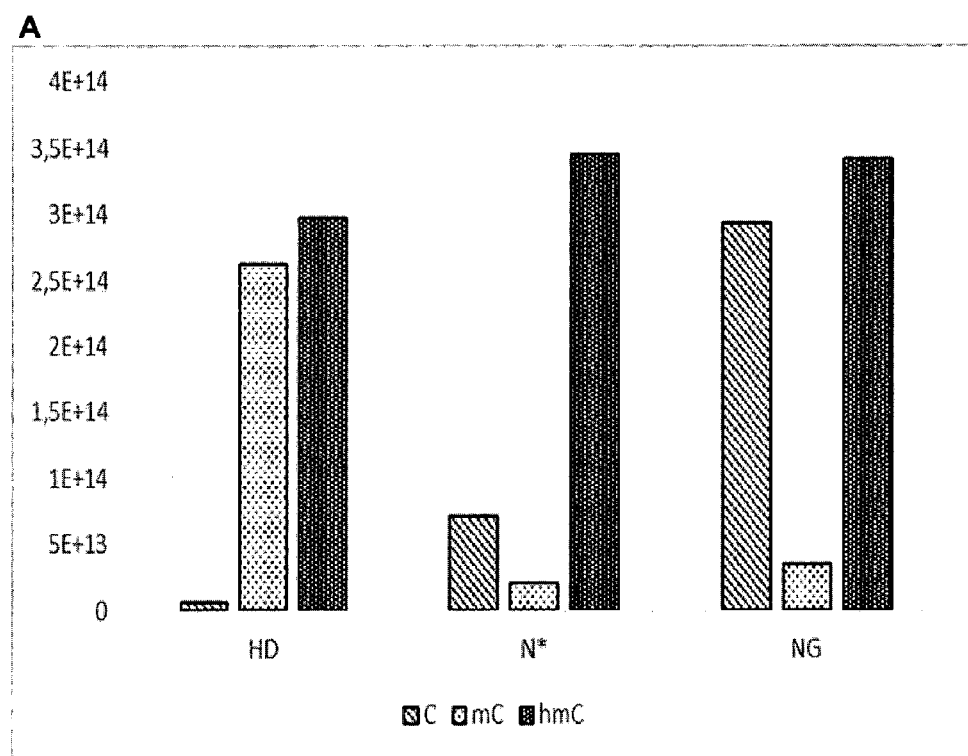
Figure 15:
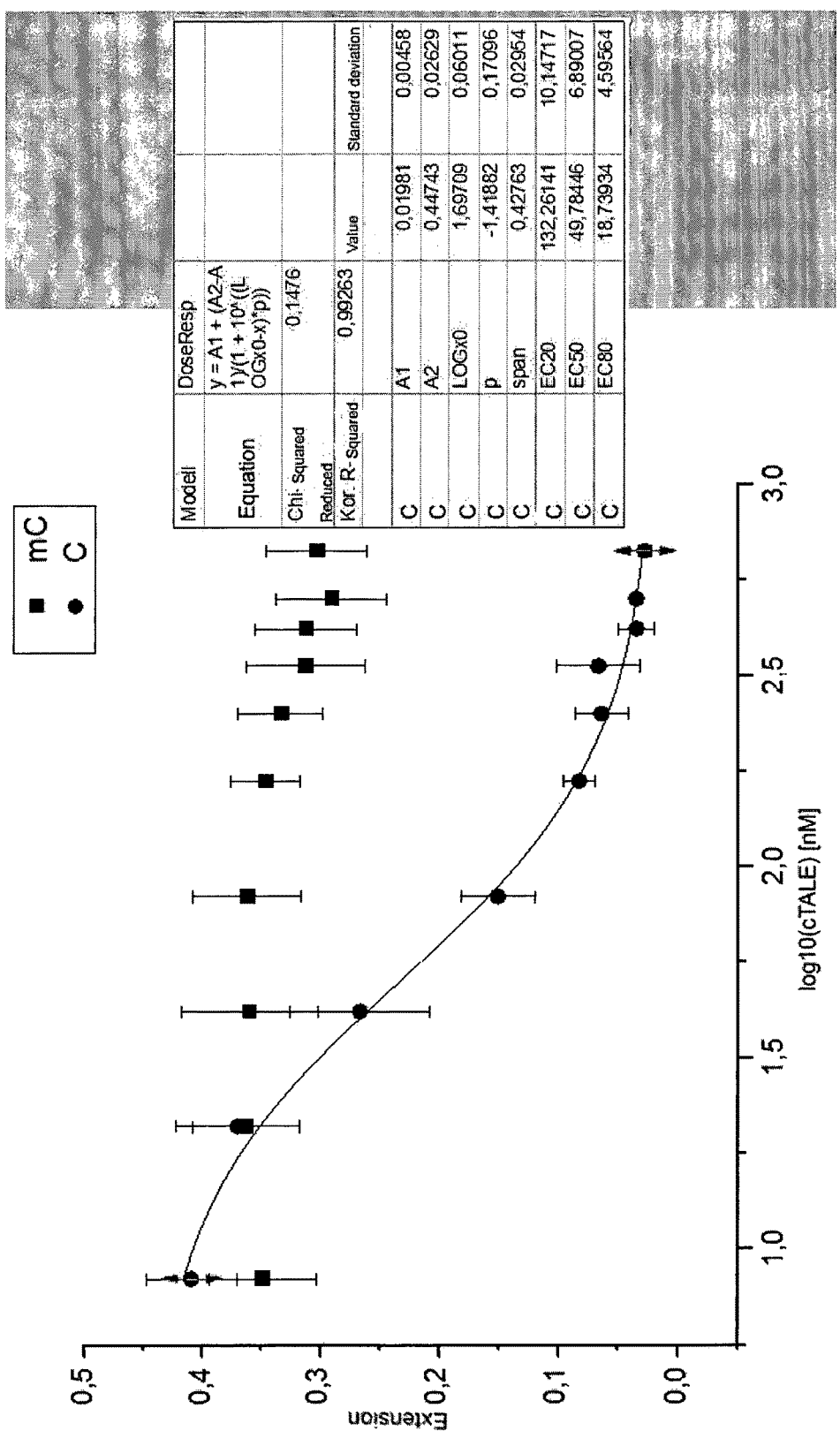
Figure 15:
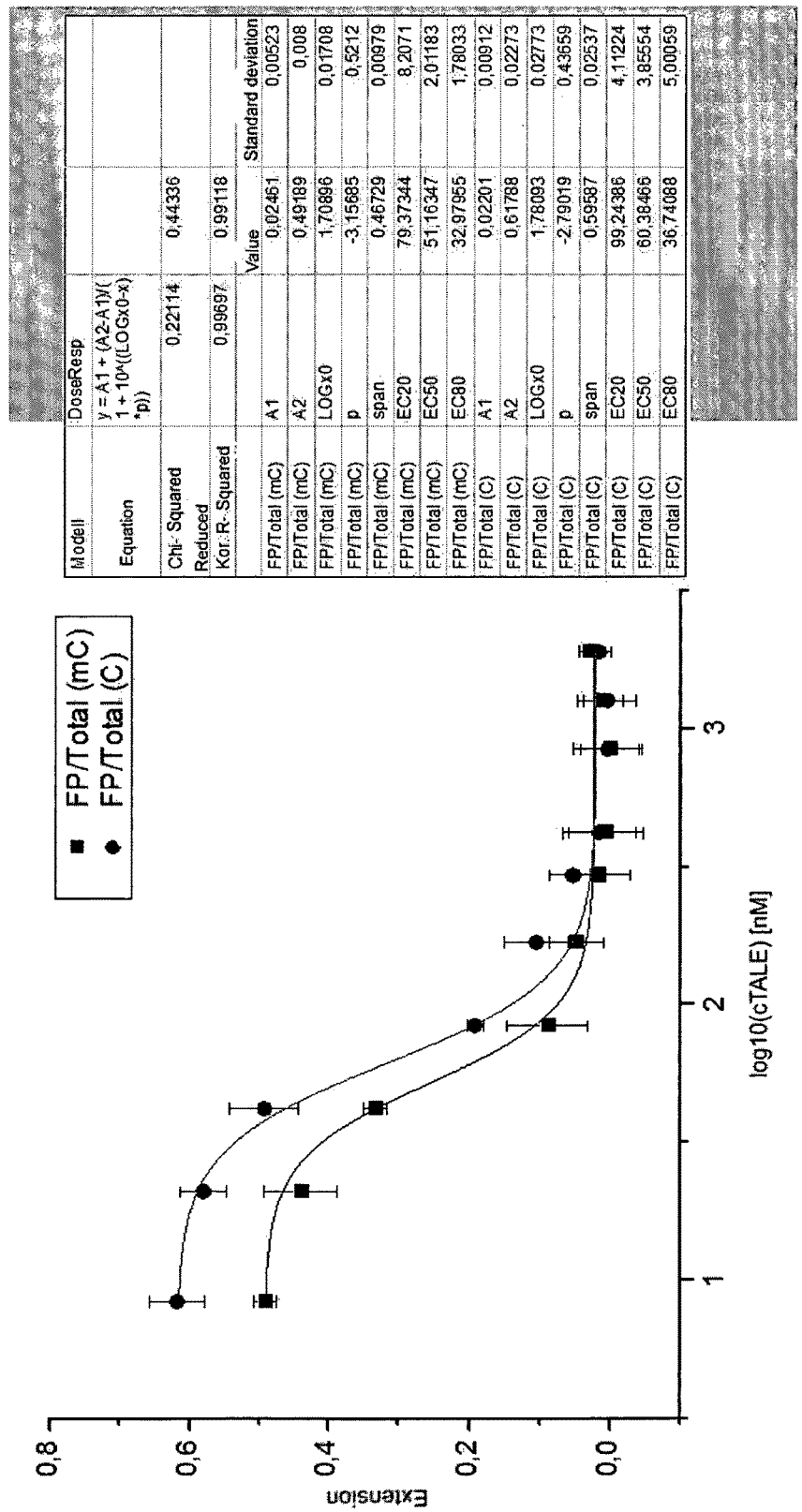
Figure 15:
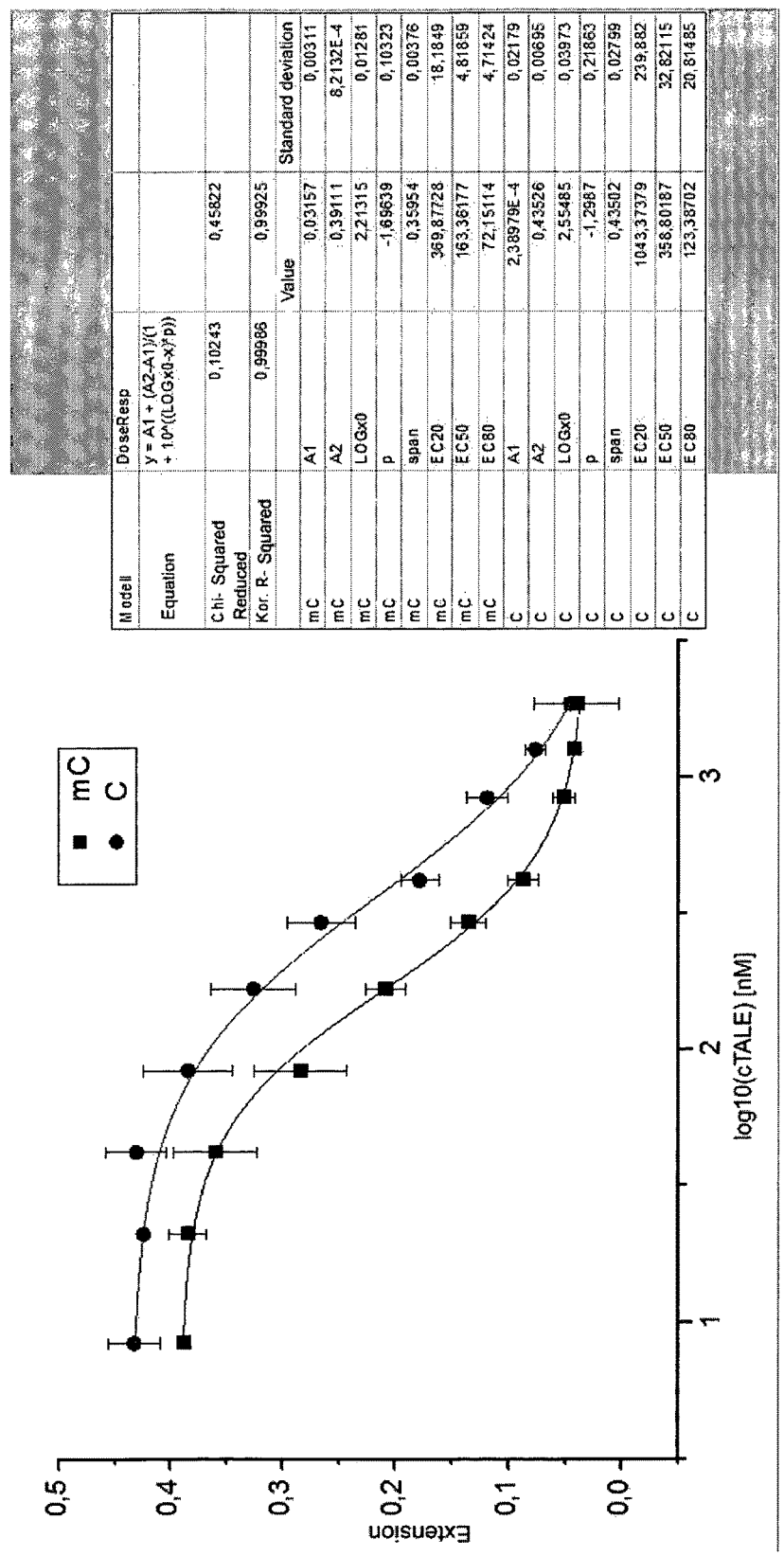

To gain quantitative insights into the $^{5m}C/^{5m}C/C$ discrimination ability of TALE_037 and TALE_038, primer extension reactions were performed with templates t97, t97_C6 mC and t97_C6 hmC with varying TALE/target DNA ratios (FIG. 15 C and Figure D).

For t97 and t97_C6 mC, primer extension declined with increasing TALE concentrations till full inhibition. TALE_037 provides a similar binding affinity to target DNA containing $^{5m}C$ and C ($IC_{50}(C)=60±4$ nM, $IC_{50}(mC)=51±2$ nM, FIG. 15C). In contrast, a reduction in primer extension efficiency for target DNA containing $^{5hm}C$ at position 6 to 50% was observed at an approximate TALE concentration of 1500 nM, confirming highly effective $^{5hm}C$ and $^{5m}C/C$ discrimination. Under use of TALE_038 primer extension for t97 and t97_C6 mC declined with increasing TALE concentrations till full inhibition but with a ~2-fold difference between $IC_{50}$ values for t97 ($IC_{50}(C)=357±33$ nM, FIG. 15D) and t97_C6 mC ($IC_{50}(mC)=163±5$ nM, FIG. 15D). Again, a reduction in primer extension efficiency for target DNA containing $^{5hm}C$ at position 6 to 50% was estimated to an approximate TALE concentration of 2000 nM, confirming highly effective $^{5hm}C/C$ and $^{5m}C$ discrimination.

Discussion:

In summary, the first application of TALE proteins is presented that enables the detection of a chemical DNA modification with high resolution. The methodology offers the direct, conversion-free detection of the status and level of $^{5m}C$-modification in a strand-specific manner, at single nucleotide positions and with excellent resolution (≤10% of the $^{5m}C$-modification level). In contrast to all proteins that have previously been employed for $^{5m}C$-discrimination, TALEs provide sufficient sequence-selectivity to be applicable in large, eukaryotic genomes and at the same time are not known to exhibit inherent sequence constraints. Combined with the universal process of enzymatic DNA synthesis as signal output, this flexibility should result in a high scope of applicable target sequences. Furthermore, the signaling strategy should enable the combination with quantitative and sensitive DNA analysis techniques that offer throughputs beyond the one of qPCR, e.g. microarrays and next generation sequencing. Finally, the availability of endogenous, programmable proteins that exhibit $^{5m}C$-sensitive DNA-binding and repressive function opens up exciting perspectives to detect $^{5m}C$ directly in, living cells and to regulate DNA-associated processes distinct from DNA replication.

Sequence Data:

The following DNA sequences are disclosed in the present application. 5-Methylcytosine nucleotides are marked as $\underline{c}$, 5-Hydroxymethylcytosine nucleotides as $\underline{c}$.

SEQ ID NO: 1
dHax_hom_KpnI_fwd (oDaS308):

```
TTT TTG GTA CCG TGG ACT TGA GGA CAC TCG GTT ATT

CGC AAC AGC
```

SEQ ID NO: 2
dHax_hom_NotI_His6_rev (oDaS231):

```
TTT TGC GGC CGC TCA GTG ATG GTG ATG GTG ATG TTC

CAG CAG ATG GTC ATT CG
```

SEQ ID NO: 3
97 (oGrK_415):

AGA CGG CAT ACG ATC TTC CGT TTC CAC ATC CAC CAC
ATC CCA ACA GAG CAG CGG GAG CAG CAG TAA AGA TCG
GAA GAG C

SEQ ID NO: 4
97_C2/5/6/11/12/14→mC (oGrK_416):

AGA CGG CAT ACG ATC TTC CGT TTC CAC ATC CAC CAC
ATC CCA ACA GAG CAG CGG GAG CAG CAG TAA AGA TCG
GAA GAG C

SEQ ID NO: 5
97_C2/5/6/11/12/14→mC_rev (oGrK_417):

GCT CTT CCG ATC TTT ACT GCT GCT CCC GCT GCT CTG
TTG GGA TGT GGT GGA TGT GGA AAC GGA AGA TCG TAT
GCC GTC T

SEQ ID NO: 6
97_T3/4/8/9/10/16→C (oGrK_418):

AGA CGG CAT ACG ATC CCC CGC CCC CAC ACC CAC CAC
ATC CCA ACA GAG CAG CGG GAG CAG CAG TAA AGA TCG
GAA GAG C

SEQ ID NO: 7
97_T3/418/9/10/16→mC (oGrK_419):

AGA CGG CAT ACG ATC CCC CGC CCC CAC ACC CAC CAC
ATC CCA ACA GAG CAG CGG GAG CAG CAG TAA AGA TCG
GAA GAG C

SEQ ID NO: 8
97_T3/4/8/9/10/16→mC_rev (oGrK_420):

GCT CTT CCG ATC TTT ACT GCT GCT CCC GCT GCT CTG
TTG GGA TGT GGT GGG TGT GGG GGC GGG GGA TCG TAT
GCC GTC T

SEQ ID NO: 9
t97 (oGrK_476):

TGG ATT CCC ACT CTT CAG CCC CAG CGT TAC AGC ATC
TTC AGT GGC TTC TTC CAC CGT GAG CTC TTC CGT TTC
CAC ATC C

SEQ ID NO: 10
t97_C6→mC (oGrK_465):

TGG ATT CCC ACT CTT CAG CCC CAG CGT TAC AGC ATC
TTC AGT GGC TTC TTC CAC CGT GAG CTC TTC CGT TTC
CAC ATC C

SEQ ID NO: 11
t97_C2→mC (oGrK_515):

TGG ATT CCC ACT CTT CAG CCC CAG CGT TAC AGC ATC
TTC AGT GGC TTC TTC CAC CGT GAG CTC TTC CGT TTC
CAC ATC C

SEQ ID NO: 12
t97_C14→mC (oGrK_516):

TGG ATT CCC ACT CTT CAG CCC CAG CGT TAC AGC ATC
TTC AGT GGC TTC TTC CAC CGT GAG CTC TTC CGT TTC
CAC ATC C

SEQ ID NO: 13
t97_C2/6→mC (oGrK_517):

TGG ATT CCC ACT CTT CAG CCC CAG CGT TAC AGC ATC
TTC AGT GGC TTC TTC CAC CGT GAG CTC TTC CGT TTC
CAC ATC C

SEQ ID NO: 14
t97_C2/6/14→mC (oGrK_518):

TGG ATT CCC ACT CTT CAG CCC CAG CGT TAC AGC ATC
TTC AGT GGC TTC TTC CAC CGT GAG CTC TTC CGT TTC
CAC ATC C

SEQ ID NO: 15
p97_rev (oGrK_466):

GGA TGT GGA AAC GGA AGA

Bio-p97_rev (oGrK_467):

5'-Biotin-GGA TGT GGA AAC GGA AGA

SEQ ID NO: 16
qp97_fwd (oGrK_621):

CCC ACT CTT CAG CCC CA

SEQ ID NO: 17
qp97_rev (oGrK_622):

GGT GGA AGA AGA GCT CAC G

SEQ ID NO: 18
t97_C6→hmC (oGrK_520):

TGG ATT CCC ACT CTT CAG CCC CAG CGT TAC AGC ATC
TTC AGT GGC TTC TTC CAC CGT GAG CTC TTC *C*GT TTC
CAC ATC C

SEQ ID NO: 19
t97_C2→hmC (oGrK_519):

TGG ATT CCC ACT CTT CAG CCC CAG CGT TAC AGC ATC
TTC AGT GGC TTC TTC CAC CGT GAG CT*C* TTC CGT TTC
CAC ATC C

SEQ ID NO: 20
t57 (oGrK_702):

ACA TTT AAA TCC AAC ATT TAA AAC GCT CCC ACT TCA
GTT CCC CAC GGT CGG TAT GGT TTA CTG CTG CTC CCG
CT

SEQ ID NO: 21
t57_C8→mC (oGrK_703):

ACA TTT AAA TCC AAC ATT TAA AAC GCT CCC ACT TCA
GTT CCC CAC GGT CGG TAT GGT TTA CTG *C*TG CTC CCG
CT

SEQ ID NO: 22
t57_C5→mC (oGrK_790):

ACA TTT AAA TCC AAC ATT TAA AAC GCT CCC ACT TCA
GTT CCC CAC GGT CGG TAT GGT TTA *C*TG CTG CTC CCG
CT

SEQ ID NO: 23
t57_C11→mC (oGrK_791):

ACA TTT AAA TCC AAC ATT TAA AAC GCT CCC ACT TCA
GTT CCC CAC GGT CGG TAT GGT TTA CTG CTG *C*TC CCG
CT

SEQ ID NO: 24
t57_C13→mC (oGrK_792):

ACA TTT AAA TCC AAC ATT TAA AAC GCT CCC ACT TCA
GTT CCC CAC GGT CGG TAT GGT TTA CTG CTG CT*C* CCG
CT

SEQ ID NO: 25
t57_C14→mC (oGrK_793):

ACA TTT AAA TCC AAC ATT TAA AAC GCT CCC ACT TCA
GTT CCC CAC GGT CGG TAT GGT TTA CTG CTG CTC *C*CG
CT

SEQ ID NO: 26
t57_C15→mC (oGrK_794):

ACA TTT AAA TCC AAC ATT TAA AAC GCT CCC ACT TCA
GTT CCC CAC GGT CGG TAT GGT TTA CTG CTG CTC C*C*G
CT

SEQ ID NO: 27
t57_C17→mC (oGrK_795):

ACA TTT AAA TCC AAC ATT TAA AAC GCT CCC ACT TCA
GTT CCC CAC GGT CGG TAT GGT TTA CTG CTG CTC CCG
*C*T

SEQ ID NO: 28
p57_rev (oGrK_787):

GCA GCG GGA GCA GCA GTA AA

The following is the amino acid sequence of TALE_97:

SEQ ID NO: 29
TALE_97:

MSDKIIHLTDDSFDTDVLKADGAILVDFWAEWCGPCKMIAPILDEIADE
YQGKLTVAKLNIDQNPGTAPKYGIRGIPTLLLFKNGEVAATKVGALSKG
QLKEFLDANLAGSGSGERQHMDSPDLGTVDLRTLGYSQQQQEKIKPKVR
STVAQHHEALVGHGFTHAHIVALSQHPAALGTVAVKYQDMIAALPEATH
EAIVGVGKQWSGARALEALLTVAGELRGPPLQLDTGQLLKIAKRGGVTA
VEAVHAWRNALTGAPLNLTPDQVVAIASHDGGKQALETVQRLLPVLCQD
HGLTPEQVVAIASNGGGKQALETVQRLLPVLCQAHGLTPDQVVAIASNG
GGKQALETVQRLLPVLCQAHGLTPAQVVAIASHDGGKQALETVQRLLPV
LCQDHGLTPDQVVAIASHDGGKQALETVQRLLPVLCQDHGLTPEQVVAI
ANNNGGKQALETVQRLLPVLCQAHGLTPDQVVAIASNGGGKQALETVQR
LLPVLCQAHGLTPAQVVAIASNGGGKQALETVQRLLPVLCQDHGLTPDQ
VVAIASNGGGKQALETVQRLLPVLCQDHGLTPEQVVAIASHDGGKQALE
TVQRLLPVLCQAHGLTPDQVVAIASHDGGKQALETVQRLLPVLCQAHGL
TPAQVVAIASNIGGKQALETVQRLLPVLCQDHGLTPDQVVAIASHDGGK
QALETVQRLLPVLCQDHGLTPEQVVAIASNIGGKQALETVQRLLPVLCQ
AHGLTPDQVVAIASNGGGKQALETVQRLLPVLCQAHGLTPAQVVAIASH
DGGKQALETVQRLLPVLCQDHGLTPEQVVAIASNGGGRPALESIVAQLS
RPDPALAALTNDHLLEHHHHHH

---

The invention claimed is:

1. A method for the differentiation of a 5-hydroxymethyl modification of a cytosine residue of interest in a nucleic acid molecule from
   (i) a 5-methyl modification of said cytosine residue of interest or
   (ii) an unmodified cytosine residue of interest,
   said method comprising the steps of:
   (a) providing a transcription-activator-like effector (TALE) protein, said TALE protein being capable of binding in a sequence- and locus- specific manner to a region of said nucleic acid molecule that includes said cytosine residue of interest, wherein a repeat variable diresidue (RVD) of said TALE protein whose position corresponds to the position of the cytosine residue of interest is a size reduced RVD; and
   (b) determining whether said TALE protein binds to said region by
   detecting a 5-hydroxymethyl modification of said cytosine residue of interest, wherein
      (i) said modification is present when said TALE protein does not bind to said region or does bind to said region with a strongly reduced affinity, and
      (ii) said modification is absent when said TALE protein binds to said region,
   said method allowing for the direct detection of a 5-hydroxymethyl modification of said cytosine residue of interest in said nucleic acid molecule.

2. The method of claim 1, wherein the repeat variable diresidue (RVD) of said TALE protein whose position corresponds to the position of the cytosine residue of interest is the RVD H* or the RVD N*.

3. The method of claim 1, wherein step (b) comprises the step of determining whether a specific DNA polymerase reaction using a primer that is capable of binding to the region of said nucleic acid molecule that includes said cytosine residue of interest is inhibited, thus indicating binding of said TALE protein to said region, said method allowing for the direct detection of a 5-hydroxymethyl modification of said cytosine residue of interest in said nucleic acid molecule.

4. The method of claim 3, wherein step (b) comprises the steps of:
   (b1) providing a primer that is capable of binding to the region of said nucleic acid molecule that includes said cytosine residue of interest;
   (b2) adding said TALE protein to a first aliquot of the nucleic acid molecule;
   (b3) performing a first specific DNA polymerase reaction with said primer using said first aliquot of the nucleic acid molecule as template, and performing a second specific DNA polymerase reaction with said primer using a second aliquot of the nucleic acid molecule as template to which no TALE protein has been added;
   (b4) determining at least one parameter, selected from the group consisting of the concentration, size, and sequence of each of the products of said first and second specific DNA polymerase reaction; and
   (b5) determining whether said TALE protein binds to said region, wherein (i) said TALE protein does not bind to said region or does bind to said region with a strongly reduced affinity when the parameter determined in step (b4) for the first specific DNA polymerase reaction does not differ significantly from the parameter detected in step (b4) for the second specific DNA polymerase reaction, and (ii) said TALE protein binds to said region when the parameter detected in step (b4) for the first specific DNA polymerase reaction differs significantly from the parameter detected in step (b4) for the second specific DNA polymerase reaction.

5. The method of claim 4, wherein in step (b4)
   (i) the concentration of the products of said first and second specific DNA polymerase reaction is determined using a method, selected from the group consisting quantitative polymerase chain reaction (qPCR), fluorescence measurements using nucleic acid binding fluorescent probes, and photometry; and/or (ii) the size of the products of said first and second specific DNA polymerase reaction is determined using a method, selected from the group consisting of polymerase chain reaction (PCR), and gel electrophoresis; and/or (iii) the sequence of the products of said first and second specific DNA polymerase reaction is determined using a method, selected from the group consisting of Sanger sequencing, pyrosequencing, microarray hybridization, next-generation sequencing methods, and next-next-generation sequencing methods.

6. The method of claim 4, further comprising the steps of:

(d) comparing the parameter detected in step (b4) for the first specific DNA polymerase reaction to one or more respective parameters obtained from nucleic acid molecules having a known degree of modification of the cytosine residue of interest; and (e) thereby determining the degree of modification of the cytosine residue of interest in the nucleic acid molecule.

7. The method of claim 1, wherein the TALE protein is coupled directly or indirectly to an affinity ligand, said method further comprising the step of:

(c) depleting nucleic acid molecules in which a 5-methyl modification of said cytosine residue of interest or said unmodified cytosine residue of interest is present via affinity chromatography using said affinity ligand;

said method allowing for the enrichment of nucleic acid molecules in which a 5-hydroxymethyl modification of said cytosine residue of interest is present.

8. The method of claim 1, wherein the TALE protein is coupled directly or indirectly to a protein having nuclease activity, said method further comprising the step of:

(c) digesting nucleic acid molecules in which a 5-methyl modification of said cytosine residue of interest or said unmodified cytosine residue of interest is present using said protein having nuclease activity;

said method allowing for the differential digestion of nucleic acid molecules in which a 5-methyl modification of said cytosine residue of interest or said unmodified cytosine residue of interest is present, wherein nucleic acid molecules in which a 5-hydroxymethyl modification of said cytosine residue of interest is present remain undigested.

* * * * *

SEQUENCE LISTING

<160> NUMBER OF SEQ ID NOS: 29

<210> SEQ ID NO 1
<211> LENGTH: 45
<212> TYPE: DNA
<213> ORGANISM: Artificial Sequence

```
<220> FEATURE:
<223> OTHER INFORMATION: Primer

<400> SEQUENCE: 1
tttttggtac cgtggacttg aggacactcg gttattcgca acagc            45

<210> SEQ ID NO 2
<211> LENGTH: 53
<212> TYPE: DNA
<213> ORGANISM: Artificial Sequence
<220> FEATURE:
<223> OTHER INFORMATION: Primer

<400> SEQUENCE: 2
ttttgcggcc gctcagtgat ggtgatggtg atgttccagc agatggtcat tcg    53

<210> SEQ ID NO 3
<211> LENGTH: 79
<212> TYPE: DNA
<213> ORGANISM: Artificial Sequence
<220> FEATURE:
<223> OTHER INFORMATION: Target DNA Sequence

<400> SEQUENCE: 3
agacggcata cgatcttccg tttccacatc caccacatcc caacagagca gcgggagcag    60
cagtaaagat cggaagagc                                                79

<210> SEQ ID NO 4
<211> LENGTH: 79
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (15)..(15)
<223> OTHER INFORMATION: 5-methylcytosine
<220> FEATURE:
<221> NAME/KEY: misc_feature
<222> LOCATION: (18)..(18)
<223> OTHER INFORMATION: 5-methylcytosine
<220> FEATURE:
<221> NAME/KEY: misc_feature
<222> LOCATION: (19)..(19)
<223> OTHER INFORMATION: 5-methylcytosine
<220> FEATURE:
<221> NAME/KEY: misc_feature
<222> LOCATION: (24)..(24)
<223> OTHER INFORMATION: 5-methylcytosine
<220> FEATURE:
<221> NAME/KEY: misc_feature
<222> LOCATION: (25)..(25)
<223> OTHER INFORMATION: 5-methylcytosine
<220> FEATURE:
<221> NAME/KEY: misc_feature
<222> LOCATION: (30)..(30)
<223> OTHER INFORMATION: 5-methylcytosine

<400> SEQUENCE: 4
agacggcata cgatcttccg tttccacatc caccacatcc caacagagca gcgggagcag    60
cagtaaagat cggaagagc                                                79

<210> SEQ ID NO 5
<211> LENGTH: 79
<212> TYPE: DNA
<213> ORGANISM: Artificial Sequence
<220> FEATURE:
<223> OTHER INFORMATION: Target DNA Sequence
```

```
<400> SEQUENCE: 5
gctcttccga tctttactgc tgctcccgct gctctgttgg gatgtggtgg atgtggaaac    60
ggaagatcgt atgccgtct                                                 79

<210> SEQ ID NO 6
<211> LENGTH: 79
<212> TYPE: DNA
<213> ORGANISM: Artificial Sequence
<220> FEATURE:
<223> OTHER INFORMATION: Target DNA Sequence

<400> SEQUENCE: 6
agacggcata cgatcccccg cccccacacc caccacatcc caacagagca gcgggagcag    60
cagtaaagat cggaagagc                                                 79

<210> SEQ ID NO 7
<211> LENGTH: 79
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (16)..(16)
<223> OTHER INFORMATION: 5-methylcytosine
<220> FEATURE:
<221> NAME/KEY: misc_feature
<222> LOCATION: (17)..(17)
<223> OTHER INFORMATION: 5-methylcytosine
<220> FEATURE:
<221> NAME/KEY: misc_feature
<222> LOCATION: (21)..(21)
<223> OTHER INFORMATION: 5-methylcytosine
<220> FEATURE:
<221> NAME/KEY: misc_feature
<222> LOCATION: (22)..(22)
<223> OTHER INFORMATION: 5-methylcytosine
<220> FEATURE:
<221> NAME/KEY: misc_feature
<222> LOCATION: (23)..(23)
<223> OTHER INFORMATION: 5-methylcytosine
<220> FEATURE:
<221> NAME/KEY: misc_feature
<222> LOCATION: (29)..(29)
<223> OTHER INFORMATION: 5-methylcytosine

<400> SEQUENCE: 7
agacggcata cgatcccccg cccccacacc caccacatcc caacagagca gcgggagcag    60
cagtaaagat cggaagagc                                                 79

<210> SEQ ID NO 8
<211> LENGTH: 79
<212> TYPE: DNA
<213> ORGANISM: Artificial Sequence
<220> FEATURE:
<223> OTHER INFORMATION: Target DNA Sequence

<400> SEQUENCE: 8
gctcttccga tctttactgc tgctcccgct gctctgttgg gatgtggtgg gtgtggggc    60 ggggatcgt atgccgtct                                                  79

<210> SEQ ID NO 9
<211> LENGTH: 79
<212> TYPE: DNA
<213> ORGANISM: Artificial Sequence
<220> FEATURE:
<223> OTHER INFORMATION: Target DNA Sequence
```

<400> SEQUENCE: 9
tggattccca ctcttcagcc ccagcgttac agcatcttca gtggcttctt ccaccgtgag    60
ctcttccgtt tccacatcc                                                 79

<210> SEQ ID NO 10
<211> LENGTH: 79
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (67)..(67)
<223> OTHER INFORMATION: 5-methylcytosine

<400> SEQUENCE: 10
tggattccca ctcttcagcc ccagcgttac agcatcttca gtggcttctt ccaccgtgag    60
ctcttccgtt tccacatcc                                                 79

<210> SEQ ID NO 11
<211> LENGTH: 79
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (63)..(63)
<223> OTHER INFORMATION: 5-methylcytosine

<400> SEQUENCE: 11
tggattccca ctcttcagcc ccagcgttac agcatcttca gtggcttctt ccaccgtgag    60
ctcttccgtt tccacatcc                                                 79

<210> SEQ ID NO 12
<211> LENGTH: 79
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (75)..(75)
<223> OTHER INFORMATION: 5-methylcytosine

<400> SEQUENCE: 12
tggattccca ctcttcagcc ccagcgttac agcatcttca gtggcttctt ccaccgtgag    60
ctcttccgtt tccacatcc                                                 79

<210> SEQ ID NO 13
<211> LENGTH: 79
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (63)..(63)
<223> OTHER INFORMATION: 5-methylcytosine
<220> FEATURE:
<221> NAME/KEY: misc_feature
<222> LOCATION: (67)..(67)
<223> OTHER INFORMATION: 5-methylcytosine

<400> SEQUENCE: 13
tggattccca ctcttcagcc ccagcgttac agcatcttca gtggcttctt ccaccgtgag    60
ctcttccgtt tccacatcc                                                 79

<210> SEQ ID NO 14
<211> LENGTH: 79
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (63)..(63)
<223> OTHER INFORMATION: 5-methylcytosine
<220> FEATURE:
<221> NAME/KEY: misc_feature
<222> LOCATION: (67)..(67)
<223> OTHER INFORMATION: 5-methylcytosine
<220> FEATURE:
<221> NAME/KEY: misc_feature
<222> LOCATION: (75)..(75)
<223> OTHER INFORMATION: 5-methylcytosine

<400> SEQUENCE: 14
tggattccca ctcttcagcc ccagcgttac agcatcttca gtggcttctt ccaccgtgag    60
ctcttccgtt tccacatcc                                                 79

<210> SEQ ID NO 15
<211> LENGTH: 18
<212> TYPE: DNA
<213> ORGANISM: Artificial Sequence
<220> FEATURE:
<223> OTHER INFORMATION: Primer

<400> SEQUENCE: 15
ggatgtggaa acggaaga                                                  18

<210> SEQ ID NO 16
<211> LENGTH: 17
<212> TYPE: DNA
<213> ORGANISM: Artificial Sequence
<220> FEATURE:
<223> OTHER INFORMATION: Primer

<400> SEQUENCE: 16
cccactcttc agcccca                                                   17

<210> SEQ ID NO 17
<211> LENGTH: 19
<212> TYPE: DNA
<213> ORGANISM: Artificial Sequence
<220> FEATURE:
<223> OTHER INFORMATION: Primer

<400> SEQUENCE: 17
ggtggaagaa gagctcacg                                                 19

<210> SEQ ID NO 18
<211> LENGTH: 79
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (67)..(67)
<223> OTHER INFORMATION: 5-hydroxymethylcytosine

<400> SEQUENCE: 18

```
tggattccca ctcttcagcc ccagcgttac agcatcttca gtggcttctt ccaccgtgag    60
ctcttccgtt tccacatcc                                                 79
```

<210> SEQ ID NO 19
<211> LENGTH: 79
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (63)..(63)
<223> OTHER INFORMATION: 5-hydroxymethylcytosine

<400> SEQUENCE: 19

```
tggattccca ctcttcagcc ccagcgttac agcatcttca gtggcttctt ccaccgtgag    60
ctcttccgtt tccacatcc                                                 79
```

<210> SEQ ID NO 20
<211> LENGTH: 74
<212> TYPE: DNA
<213> ORGANISM: Artificial Sequence
<220> FEATURE:
<223> OTHER INFORMATION: Target DNA Sequence

<400> SEQUENCE: 20

```
acatttaaat ccaacattta aaacgctccc acttcagttc cccacggtcg gtatggttta    60
ctgctgctcc cgct                                                      74
```

<210> SEQ ID NO 21
<211> LENGTH: 74
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (64)..(64)
<223> OTHER INFORMATION: 5-methylcytosine

<400> SEQUENCE: 21

```
acatttaaat ccaacattta aaacgctccc acttcagttc cccacggtcg gtatggttta    60
ctgctgctcc cgct                                                      74
```

<210> SEQ ID NO 22
<211> LENGTH: 74
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (61)..(61)
<223> OTHER INFORMATION: 5-methylcytosine

<400> SEQUENCE: 22

```
acatttaaat ccaacattta aaacgctccc acttcagttc cccacggtcg gtatggttta    60
ctgctgctcc cgct                                                      74
```

<210> SEQ ID NO 23
<211> LENGTH: 74
<212> TYPE: DNA
<213> ORGANISM: Artificial Sequence
<220> FEATURE:

<223> OTHER INFORMATION: Target DNA Sequence
<220> FEATURE:
<221> NAME/KEY: misc_feature
<222> LOCATION: (67)..(67)
<223> OTHER INFORMATION: 5-methylcytosine

<400> SEQUENCE: 23
acatttaaat ccaacattta aaacgctccc acttcagttc cccacggtcg gtatggttta    60
ctgctgctcc cgct    74

<210> SEQ ID NO 24
<211> LENGTH: 74
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (69)..(69)
<223> OTHER INFORMATION: 5-methylcytosine

<400> SEQUENCE: 24
acatttaaat ccaacattta aaacgctccc acttcagttc cccacggtcg gtatggttta    60
ctgctgctcc cgct    74

<210> SEQ ID NO 25
<211> LENGTH: 74
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (70)..(70)
<223> OTHER INFORMATION: 5-methylcytosine

<400> SEQUENCE: 25
acatttaaat ccaacattta aaacgctccc acttcagttc cccacggtcg gtatggttta    60
ctgctgctcc cgct    74

<210> SEQ ID NO 26
<211> LENGTH: 74
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (71)..(71)
<223> OTHER INFORMATION: 5-methylcytosine

<400> SEQUENCE: 26
acatttaaat ccaacattta aaacgctccc acttcagttc cccacggtcg gtatggttta    60
ctgctgctcc cgct    74

<210> SEQ ID NO 27
<211> LENGTH: 74
<212> TYPE: DNA
<213> ORGANISM: Artificial Sequence
<220> FEATURE:
<223> OTHER INFORMATION: Target DNA Sequence
<220> FEATURE:
<221> NAME/KEY: misc_feature
<222> LOCATION: (73)..(73)
<223> OTHER INFORMATION: 5-methylcytosine

<400> SEQUENCE: 27

```
acatttaaat ccaacattta aaacgctccc acttcagttc cccacggtcg gtatggttta    60
ctgctgctcc cgct                                                      74
```

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28

```
gcagcgggag cagcagtaaa                                                20
```

<210> SEQ ID NO 29
<211> LENGTH: 855
<212> TYPE: PRT
<213> ORGANISM: Artificial Sequence
<220> FEATURE:
<223> OTHER INFORMATION: TALE protein

<400> SEQUENCE: 29

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly Glu Arg Gln His Met Asp Ser Pro Asp Leu Gly Thr Val Asp
        115                 120                 125

Leu Arg Thr Leu Gly Tyr Ser Gln Gln Gln Gln Glu Lys Ile Lys Pro
    130                 135                 140

Lys Val Arg Ser Thr Val Ala Gln His His Glu Ala Leu Val Gly His
145                 150                 155                 160

Gly Phe Thr His Ala His Ile Val Ala Leu Ser Gln His Pro Ala Ala
                165                 170                 175

Leu Gly Thr Val Ala Val Lys Tyr Gln Asp Met Ile Ala Ala Leu Pro
            180                 185                 190

Glu Ala Thr His Glu Ala Ile Val Gly Val Gly Lys Gln Trp Ser Gly
        195                 200                 205

Ala Arg Ala Leu Glu Ala Leu Leu Thr Val Ala Gly Glu Leu Arg Gly
    210                 215                 220

Pro Pro Leu Gln Leu Asp Thr Gly Gln Leu Leu Lys Ile Ala Lys Arg
225                 230                 235                 240

Gly Gly Val Thr Ala Val Glu Ala Val His Ala Trp Arg Asn Ala Leu
                245                 250                 255

Thr Gly Ala Pro Leu Asn Leu Thr Pro Asp Gln Val Val Ala Ile Ala
            260                 265                 270

Ser His Asp Gly Gly Lys Gln Ala Leu Glu Thr Val Gln Arg Leu Leu
```

```
            275                 280                 285
Pro Val Leu Cys Gln Asp His Gly Leu Thr Pro Glu Gln Val Val Ala
290                 295                 300

Ile Ala Ser Asn Gly Gly Lys Gln Ala Leu Glu Thr Val Gln Arg
305                 310                 315                 320

Leu Leu Pro Val Leu Cys Gln Ala His Gly Leu Thr Pro Asp Gln Val
                325                 330                 335

Val Ala Ile Ala Ser Asn Gly Gly Lys Gln Ala Leu Glu Thr Val
        340                 345                 350

Gln Arg Leu Leu Pro Val Leu Cys Gln Ala His Gly Leu Thr Pro Ala
                355                 360                 365

Gln Val Val Ala Ile Ala Ser His Asp Gly Gly Lys Gln Ala Leu Glu
    370                 375                 380

Thr Val Gln Arg Leu Leu Pro Val Leu Cys Gln Asp His Gly Leu Thr
385                 390                 395                 400

Pro Asp Gln Val Val Ala Ile Ala Ser His Asp Gly Gly Lys Gln Ala
                405                 410                 415

Leu Glu Thr Val Gln Arg Leu Leu Pro Val Leu Cys Gln Asp His Gly
            420                 425                 430

Leu Thr Pro Glu Gln Val Val Ala Ile Ala Asn Asn Asn Gly Gly Lys
            435                 440                 445

Gln Ala Leu Glu Thr Val Gln Arg Leu Leu Pro Val Leu Cys Gln Ala
450                 455                 460

His Gly Leu Thr Pro Asp Gln Val Val Ala Ile Ala Ser Asn Gly Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Ala Gln Val Val Ala Ile Ala Ser Asn
                500                 505                 510

Gly Gly Gly Lys Gln Ala Leu Glu Thr Val Gln Arg Leu Leu Pro Val
            515                 520                 525

Leu Cys Gln Asp His Gly Leu Thr Pro Asp Gln Val Val Ala Ile Ala
530                 535                 540

Ser Asn Gly Gly Gly Lys Gln Ala Leu Glu Thr Val Gln Arg Leu Leu
545                 550                 555                 560

Pro Val Leu Cys Gln Asp His Gly Leu Thr Pro Glu Gln Val Val Ala
                565                 570                 575

Ile Ala Ser His Asp Gly Gly Lys Gln Ala Leu Glu Thr Val Gln Arg
            580                 585                 590

Leu Leu Pro Val Leu Cys Gln Ala His Gly Leu Thr Pro Asp Gln Val
            595                 600                 605

Val Ala Ile Ala Ser His Asp Gly Gly Lys Gln Ala Leu Glu Thr Val
        610                 615                 620

Gln Arg Leu Leu Pro Val Leu Cys Gln Ala His Gly Leu Thr Pro Ala
625                 630                 635                 640

Gln Val Val Ala Ile Ala Ser Asn Ile Gly Gly Lys Gln Ala Leu Glu
                645                 650                 655

Thr Val Gln Arg Leu Leu Pro Val Leu Cys Gln Asp His Gly Leu Thr
            660                 665                 670

Pro Asp Gln Val Val Ala Ile Ala Ser His Asp Gly Gly Lys Gln Ala
            675                 680                 685

Leu Glu Thr Val Gln Arg Leu Leu Pro Val Leu Cys Gln Asp His Gly
690                 695                 700
```

```
Leu Thr Pro Glu Gln Val Val Ala Ile Ala Ser Asn Ile Gly Gly Lys
705                 710                 715                 720

Gln Ala Leu Glu Thr Val Gln Arg Leu Leu Pro Val Leu Cys Gln Ala
                725                 730                 735

His Gly Leu Thr Pro Asp Gln Val Val Ala Ile Ala Ser Asn Gly Gly
            740                 745                 750

Gly Lys Gln Ala Leu Glu Thr Val Gln Arg Leu Leu Pro Val Leu Cys
        755                 760                 765

Gln Ala His Gly Leu Thr Pro Ala Gln Val Val Ala Ile Ala Ser His
    770                 775                 780

Asp Gly Gly Lys Gln Ala Leu Glu Thr Val Gln Arg Leu Leu Pro Val
785                 790                 795                 800

Leu Cys Gln Asp His Gly Leu Thr Pro Glu Gln Val Val Ala Ile Ala
                805                 810                 815

Ser Asn Gly Gly Gly Arg Pro Ala Leu Glu Ser Ile Val Ala Gln Leu
                820                 825                 830

Ser Arg Pro Asp Pro Ala Leu Ala Ala Leu Thr Asn Asp His Leu Leu
        835                 840                 845

Glu His His His His His His
    850                 855
```